(12) United States Patent
Frith

(10) Patent No.: US 7,607,839 B2
(45) Date of Patent: Oct. 27, 2009

(54) MEDICAL LIGHT SOURCE AND METHOD

(75) Inventor: Martin A. Frith, Goleta, CA (US)

(73) Assignee: Linvatec Corporation, Largo, FL (US)

( * ) Notice: Subject to any disclaimer, the term of this patent is extended or adjusted under 35 U.S.C. 154(b) by 0 days.

(21) Appl. No.: 12/315,409

(22) Filed: Dec. 3, 2008

(65) Prior Publication Data

US 2009/0087149 A1 Apr. 2, 2009

Related U.S. Application Data

(62) Division of application No. 11/725,717, filed on Mar. 20, 2007, now Pat. No. 7,500,791.

(51) Int. Cl.
*G02B 6/36* (2006.01)
*G02B 6/38* (2006.01)

(52) U.S. Cl. .............................. 385/88; 385/53; 385/58

(58) Field of Classification Search .................. 385/88, 385/53, 58
See application file for complete search history.

(56) References Cited

U.S. PATENT DOCUMENTS

| 4,186,998 | A | * | 2/1980 | Holzman | 385/73 |
|---|---|---|---|---|---|
| 4,376,566 | A | * | 3/1983 | Blackington | 385/19 |
| 4,469,098 | A | * | 9/1984 | Davi | 606/7 |
| 4,633,872 | A | * | 1/1987 | Chaffee et al. | 606/11 |
| 4,863,267 | A | * | 9/1989 | Bendickson et al. | 356/155 |
| 5,076,660 | A | * | 12/1991 | Messinger | 385/119 |
| 5,509,096 | A | * | 4/1996 | Easley | 385/89 |
| 6,264,374 | B1 | * | 7/2001 | Selfridge et al. | 385/78 |
| 6,663,296 | B1 | * | 12/2003 | Blair et al. | 385/92 |
| 7,121,736 | B2 | * | 10/2006 | Ayame | 385/81 |
| 2001/0026657 | A1 | * | 10/2001 | Kodeda et al. | 385/31 |
| 2004/0179787 | A1 | * | 9/2004 | Glazowski et al. | 385/76 |
| 2005/0117849 | A1 | * | 6/2005 | Ayame | 385/53 |

* cited by examiner

*Primary Examiner*—K. Cyrus Kianni

(57) ABSTRACT

The present invention provides an apparatus and method for securing a light guide to a light source. The light guide has an end termination having a predetermined size and the light source has an opening with an axis for receiving the end termination. The opening is adaptable to receive and grip light guides of different sizes. In one aspect of the invention, an actuator is operable to expand and shrink the opening. In another aspect of the invention, one or more shields are provided to block light from exiting the light source except when a light guide is connected to the light source.

11 Claims, 21 Drawing Sheets

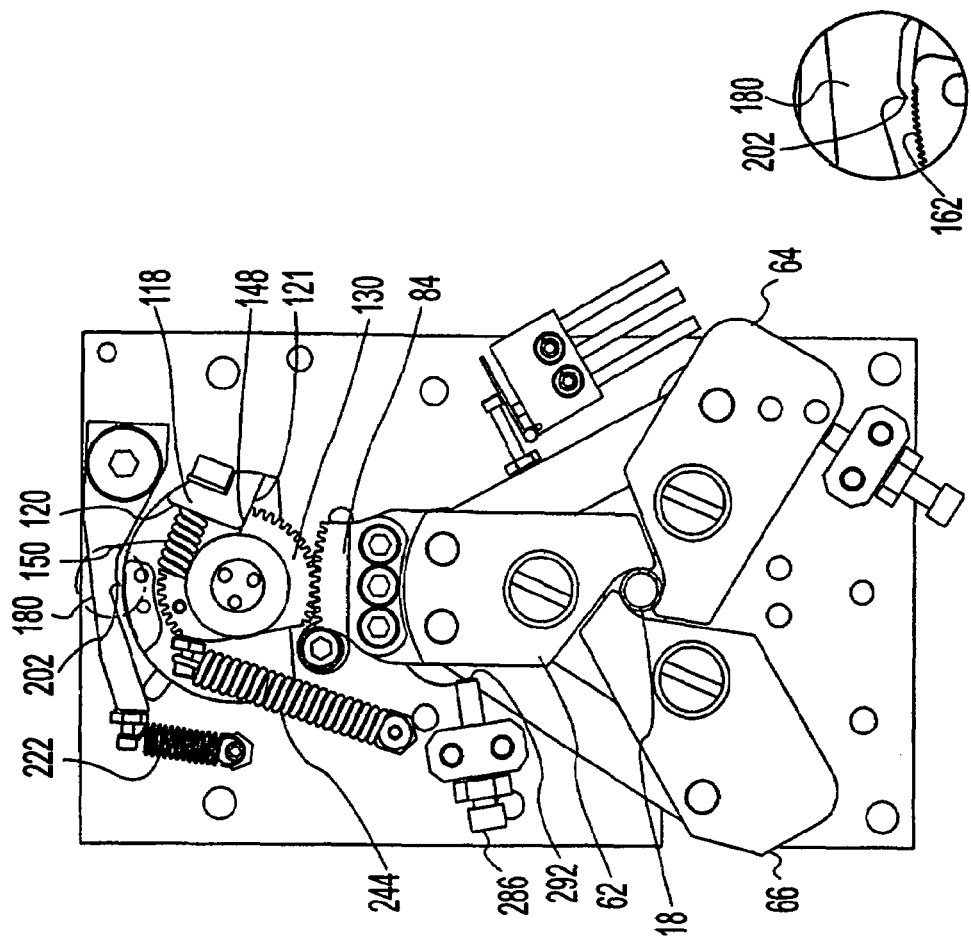
Fig. 11A
Fig. 11
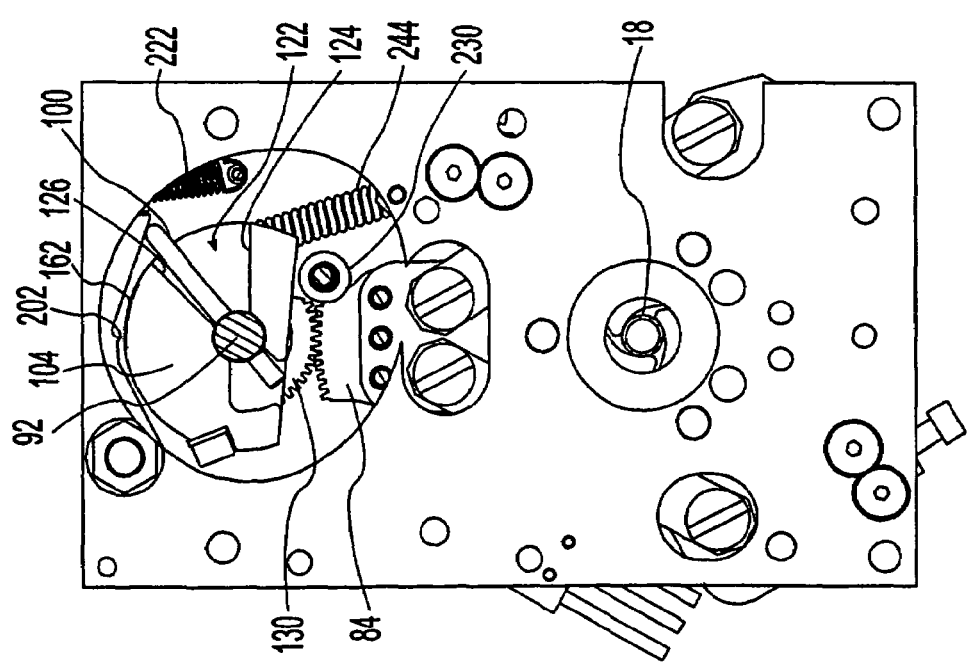
Fig. 10

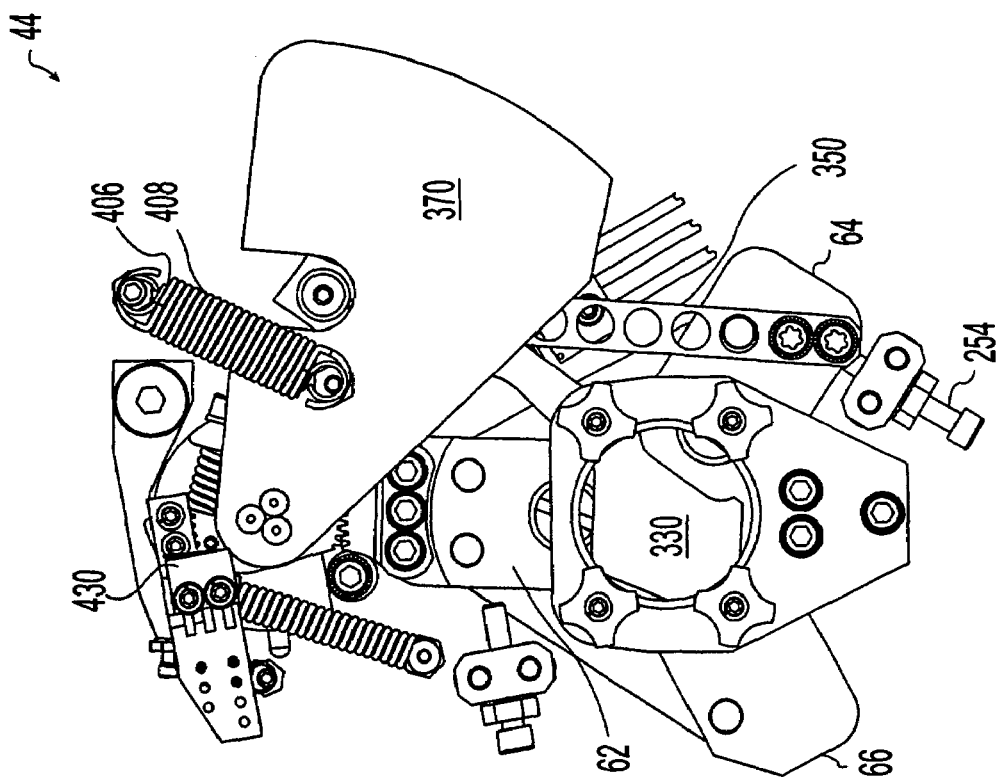
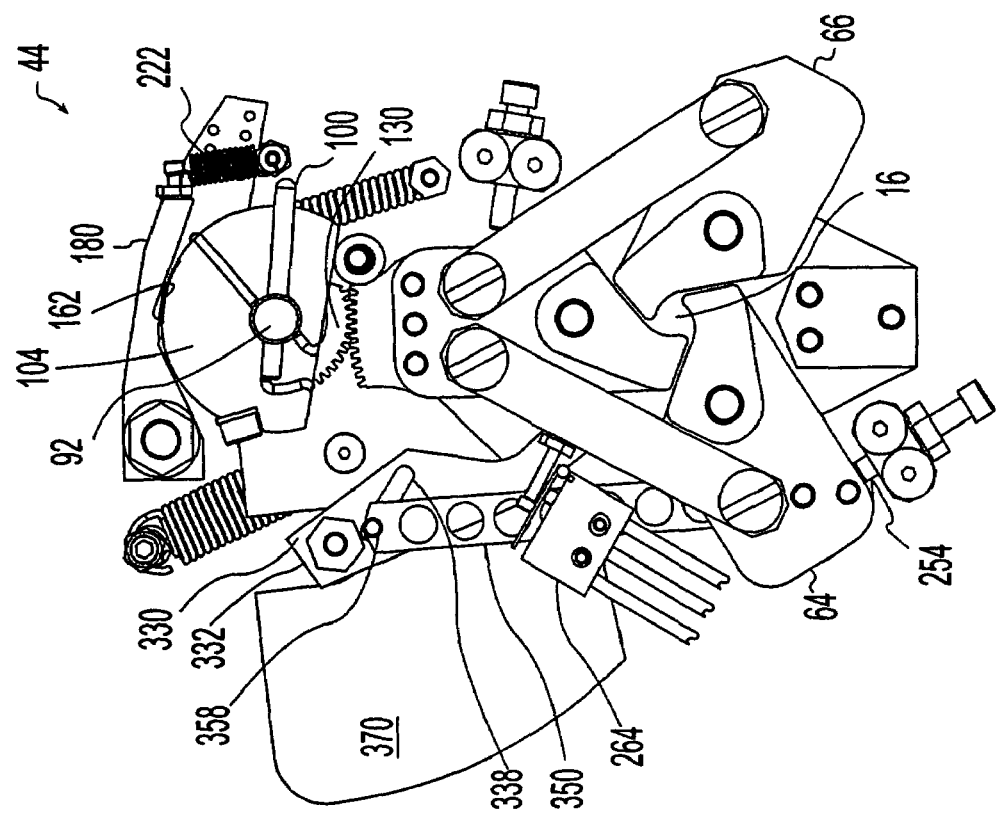
Fig. 18
Fig. 17

MEDICAL LIGHT SOURCE AND METHOD

PREVIOUS INVENTION

This application is a divisional of U.S. application Ser. No. 11/725,717, filed on Mar. 20, 2007 now U.S. Pat. No. 7,500,791.

FIELD OF THE INVENTION

The invention relates to light sources for medical procedures. In particular, the invention relates to high intensity light sources having a light guide receptacle for coupling to a light guide.

BACKGROUND

Many medical procedures require supplemental lighting in order to facilitate visualization of the treatment site. For example, minimally invasive and endoscopic techniques are typically performed with narrow light guides that deliver light from a light source to the surgical site. One end of the light guide is coupled to the light source at a light guide receptacle and another end of the light guide is connected to a medical instrument or positioned independently to illuminate the treatment site. A variety of types and sizes of light guides are provided for different applications and by different equipment manufacturers. A light guide receptacle that can accommodate different light guides is desirable.

During a medical procedure, the light guide may be repositioned, pulled, and or other wise manipulated. A light guide receptacle that provides simple coupling and uncoupling of the light guide to the light source and that grips the light guide securely is desirable.

The light source produces high intensity light that can irritate or even damage a users eyes if it is viewed directly. A light source that prevents inadvertent exposure of the user to high intensity light during coupling and uncoupling of the light guide is desirable.

SUMMARY

The present invention provides an apparatus for securing a light guide to a light source. The light guide has an end termination having a predetermined size and the light source has an opening with an axis for receiving the end termination.

In one aspect of the invention, the apparatus includes a plurality of jaws mounted for radial movement relative to the axis of the opening. The jaws are movable between an open position, a closed position, and a locked position. A control is operably connected to the jaws for moving the jaws between the closed and locked positions.

In another aspect of the invention, a medical light source includes a light guide receptacle defining an opening with a perimeter. The opening perimeter is expandable and shrinkable between an open condition in which the opening is larger than the light guide, a closed condition in which the opening is the same size as the light guide and the perimeter of the opening grips the light guide with a first gripping pressure, and a locked condition in which the perimeter of the opening grips the light guide with a second, greater gripping pressure. An actuator is operably connected to the light guide receptacle and is responsive to a user input to lock the opening perimeter in the locked condition.

In another aspect of the invention, one or more shields are provided to block light from exiting the light source except when a light guide is connected to the light source.

In another aspect of the invention, a method for securing a light guide to a light source includes expanding the opening from a rest condition, corresponding to a nominal condition of the opening with no user input and no light guide engaged with the opening, to an open condition; inserting the light guide into the opening; shrinking the opening to a closed position to grip the light guide with a first gripping pressure; increasing the gripping pressure to a second gripping pressure; and locking the opening in a locked condition to maintain the second gripping pressure without continued user input.

In another aspect of the invention, method includes positioning one or more shields to block light from exiting the light source except when a light guide is connected to the light source.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 5a is a front plan view of a portion of the assembly of FIG. 5;

FIG. 10 is a front plan view of the partially assembled light guide receptacle of FIG. 3 at the same stage of assembly as depicted in FIG. 9 with a portion of the mounting plate cut away to better reveal the mechanism;

FIG. 11 is a back plan view of the partially assembled light guide receptacle of FIG. 3 at the same stage of assembly as depicted in FIG. 9;

FIG. 11a is a detail view of a portion of the assembly of FIG. 11;

FIG. 17 is a front plan view of the fully assembled light guide receptacle of FIG. 3 (with certain elements omitted to aid visualization) in one operating position;

FIG. 18 is a back plan view of the fully assembled light guide receptacle of FIG. 3 in the same operating position as FIG. 17;

DESCRIPTION OF THE ILLUSTRATIVE EXAMPLES

Figure 1:
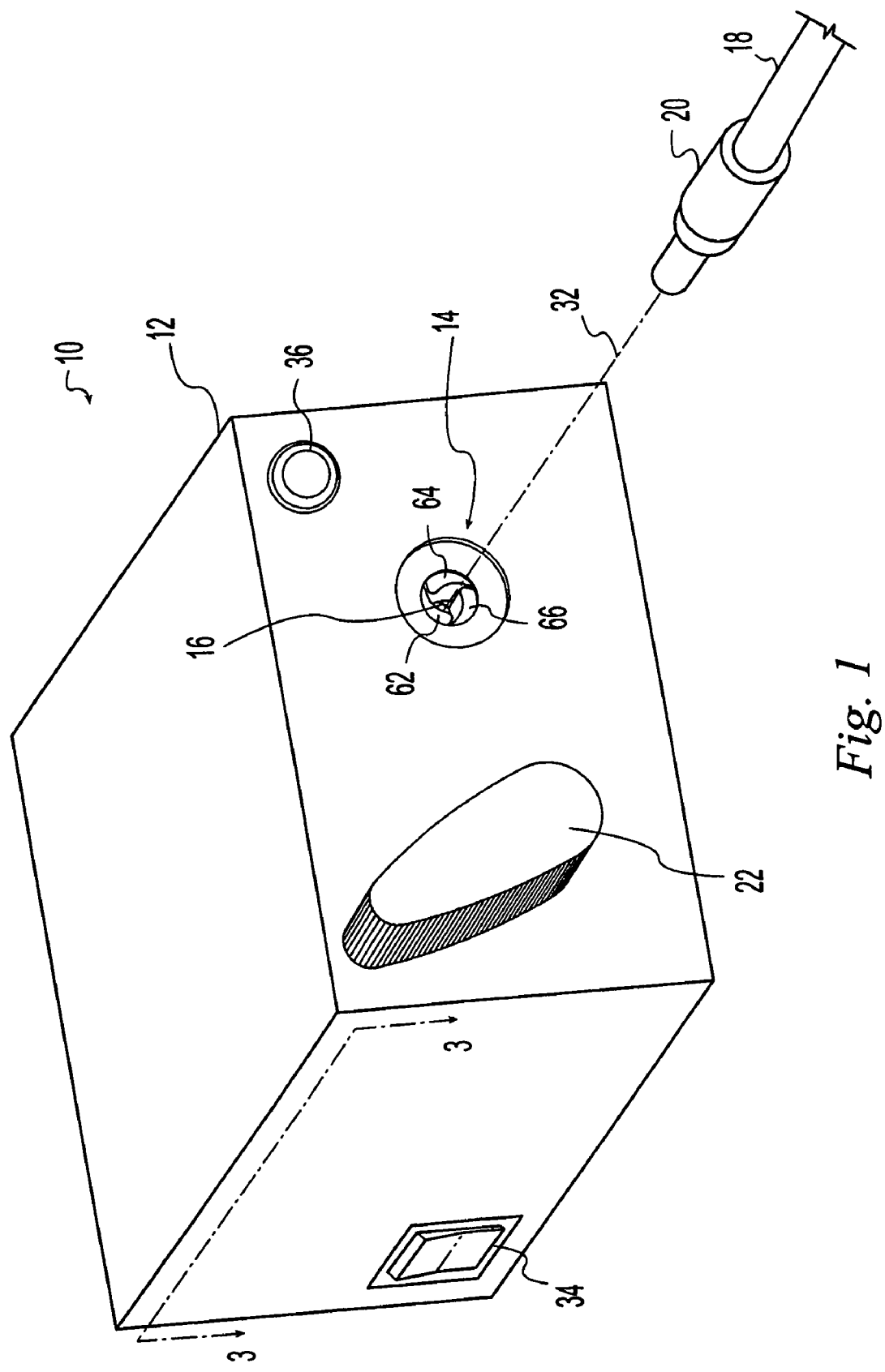
FIG. 1 is a perspective view of a light source according to the present invention.
Figure 2:
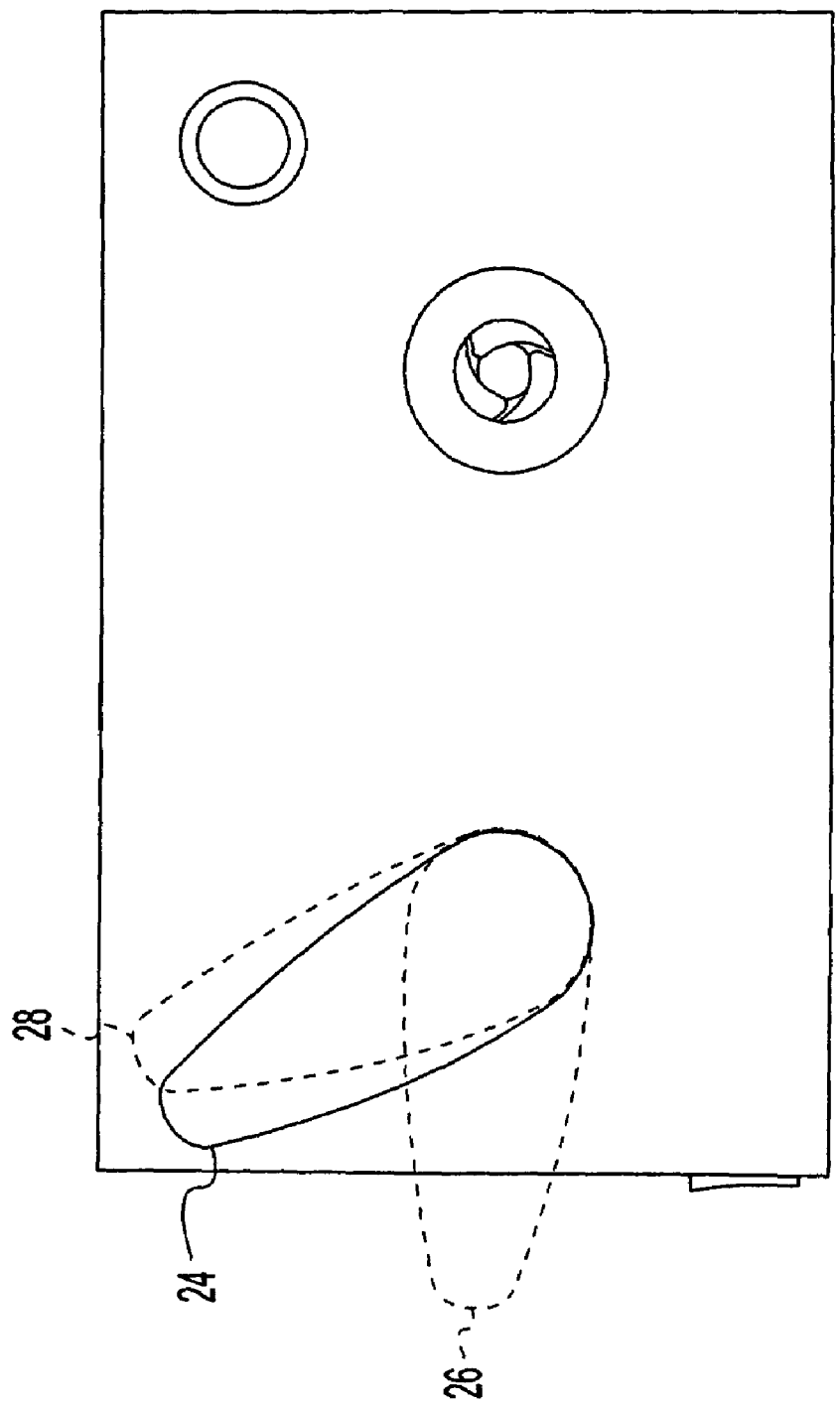
FIG. 2 is a front view of the light source of FIG. 1.

Referring to FIG. 1, embodiments of a medical light source 10 may include a housing 12 mounting a light guide receptacle 14. The light guide receptacle 14 may include an adaptable opening 16 for receiving a light guide 18. The light guide 18 may be coupled to the light guide receptacle 14 directly. The light guide 18 may be joined to a light guide terminal 20 which may be coupled to the light guide receptacle 14. The light guide receptacle opening 16 may be adaptable to receive light guides 18 and/or light guide terminals 20 of different shapes and/or sizes. The opening 16 may be operably connected to an actuator 22. The actuator 22 may be responsive to a user input to cause the opening 16 to change size and/or shape to release, grip, and/or tighten on differently sized and/or shaped light guides 18. For example, the actuator may be mounted for movement (FIG. 2) such that moving the actuator from a first position 24 to a second position 26 expands the opening 16 to permit insertion of a light guide 18. The actuator may be responsive to movement back toward the first position 24 to cause the opening to shrink and grip the light guide 18. In some embodiments, the actuator and opening may be manually moved back toward the first position by the user. In other embodiments, the actuator and opening may be moved back automatically such as by a spring, pneumatic cylinder, solenoid, motor, and/or some other suitable mechanism. The actuator 22 may be mounted for rotation, translation, and/or any other suitable movement to adjust the opening 16.

The actuator may be movable to a third position 28 in which it is operative to cause the gripping force of the opening 16 on the light guide 18 to increase. The actuator may be moved by the user or it may be moved automatically to the third position 28. Alternatively, a separate actuator and/or mechanism may be provided to cause the gripping force of the opening 16 on the light guide 18 to increase.

In some embodiments the opening 16 may include a plurality of jaws 62, 64, 66 defining the opening 16 size and being movable radially relative to the axis 32 of the opening to change the size of the opening 16. The jaws 62, 64, 66 may be mounted for translation and/or rotation.

The light source 10 may include an on/off switch 34 operably connected to a light producing element. The light source 10 may also include one or more indicators 36 for indicating the status of the opening 16, the light producing element, internal shutters, and/or any other parameter of the light source. The indicator may include an indicator light, audible tone, pictorial display, text display, and/or any other suitable indicator. For example, the indicator may be configured to indicate whether or not a light guide is inserted into the opening 16, whether or not the opening 16 is gripping a light guide, and/or whether or not the opening 16 is in the tightened position. Similarly, the indicator may be configured to indicate whether the actuator is in the first, second, or third positions 24, 26, 28.

Figure 3:
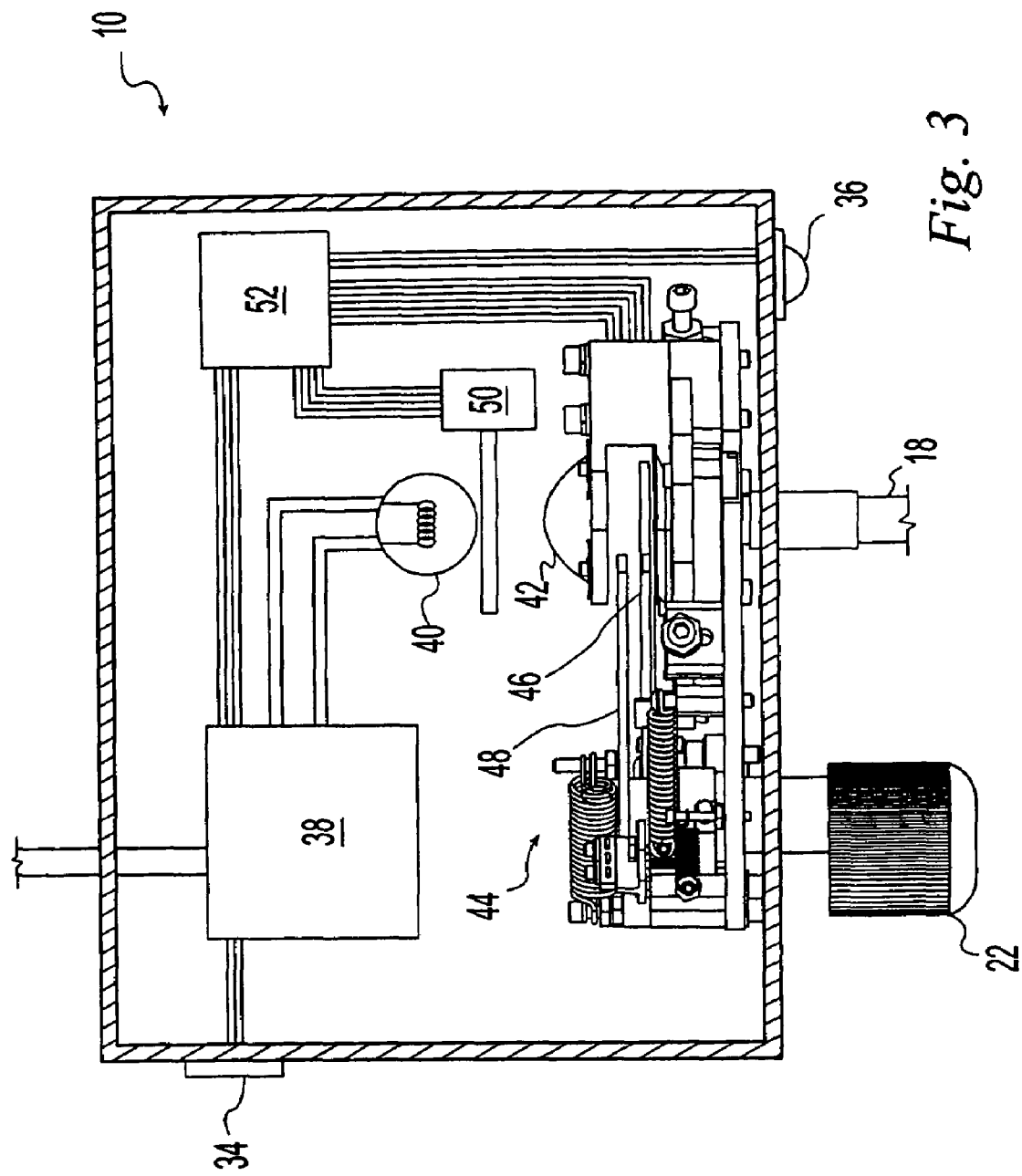
FIG. 3 is a top sectional view of the light source of FIG. 1 taken along line 3-3 of FIG. 1 and revealing the internal layout of the light source including a light guide receptacle mechanism.

FIG. 3 illustrates an exemplary layout of one embodiment of the light source 10. The light source 10 may include a power supply 38, a light producing element 40, a lens 42, a light guide receptacle mechanism 44, and/or other suitable elements. The light producing element 40 may be driven by the power source to produce light that is focused by the lens 42 into the light guide 18. The light source 10 may include a first shield 46 movable between a first position in which it blocks light from the light producing element from reaching the opening 16 and a second position in which it allows light to reach the opening 16. The first shield 46 may be operably connected to the light guide receptacle mechanism 44 to block the opening 16 when no light guide 18 is coupled to the light guide receptacle 14 and to not block the opening 16 when a light guide 18 is coupled to the light guide receptacle 14.

The light source 10 may include a second shield 48 also movable between a first position in which it blocks light from the light producing element from reaching the opening 16 and a second position in which it allows light to reach the opening 16. The second shield 48 may be operably connected to the actuator and/or light guide receptacle 14 to cooperate with the first shield 46 such that one of the first and second shields 46, 48 blocks the opening 16 unless a light guide 18 is gripped in the opening 16. For example, one or both of the shields 46, 48 may block the opening 16 when no light guide is received in the opening 16, one or both of the shields may block the opening 16 when the actuator 22 is moved to the second position 26 to expand the opening, and both of the shields may allow light to pass when the opening 16 is engaged with a light guide 18 and the actuator is released. In this way the, shields 46, 48 prevent light from exiting the opening 16 unless a light guide 18 is engaged and thus no light is permitted to strike a users eye due to leakage at the opening 16.

The light source 10 may include a shutter 50 positioned between the light producing element 40 and the opening 16 to control the amount of light transmitted to the opening 16. The shutter 50 may be adjustable to reduce the light output to a predetermined value. The shutter 50 may be adjustable between discrete light output settings and/or it may be continuously adjustable between a maximum output setting and a minimum output setting. The shutter 50 may be adjustable between a position in which it does not block any light and a position in which it blocks all light output. The shutter 50 may be operably connected to the actuator 22 and/or light guide receptacle 14 to open in response to jaw movement and/or a light guide 18 being present in the opening 16.

The light source 10 may include a microcontroller 52 operably connected to one or more elements of the light source 10 to control their operation. For example, the microcontroller may control the power supply 38, light producing element 40, shutter 50, indicator 36, elements of the light guide receptacle 14, and/or other elements of the light source 10.

FIGS. 4-28 depict an illustrative embodiment of the light guide receptacle mechanism 44. The drawings include a series of perspective exploded views and plan views illustrating how the mechanism is assembled to illustrate all of the elements of the mechanism 44, including those that are hidden in the fully assembled condition. The terms clockwise and counterclockwise are used to describe the rotation of objects as viewed from the front of the light source 10. FIGS. 4-11 depict in detail the elements of the illustrative embodiment that provide the jaw gripping and locking functions of the embodiment. FIGS. 12-16 depict the additional elements that provide the light shielding functions of the embodiment. The gripping, locking, shielding, and sensing aspects of the invention can be utilized independently from one another or they can be used in any combination. The illustrative embodiment depicts a mechanism incorporating all of these features. FIGS. 17-28 show the mechanism in different states of operation, with some of the elements omitted to aid visualization, to illustrate the features of the invention in use.

Figure 4:
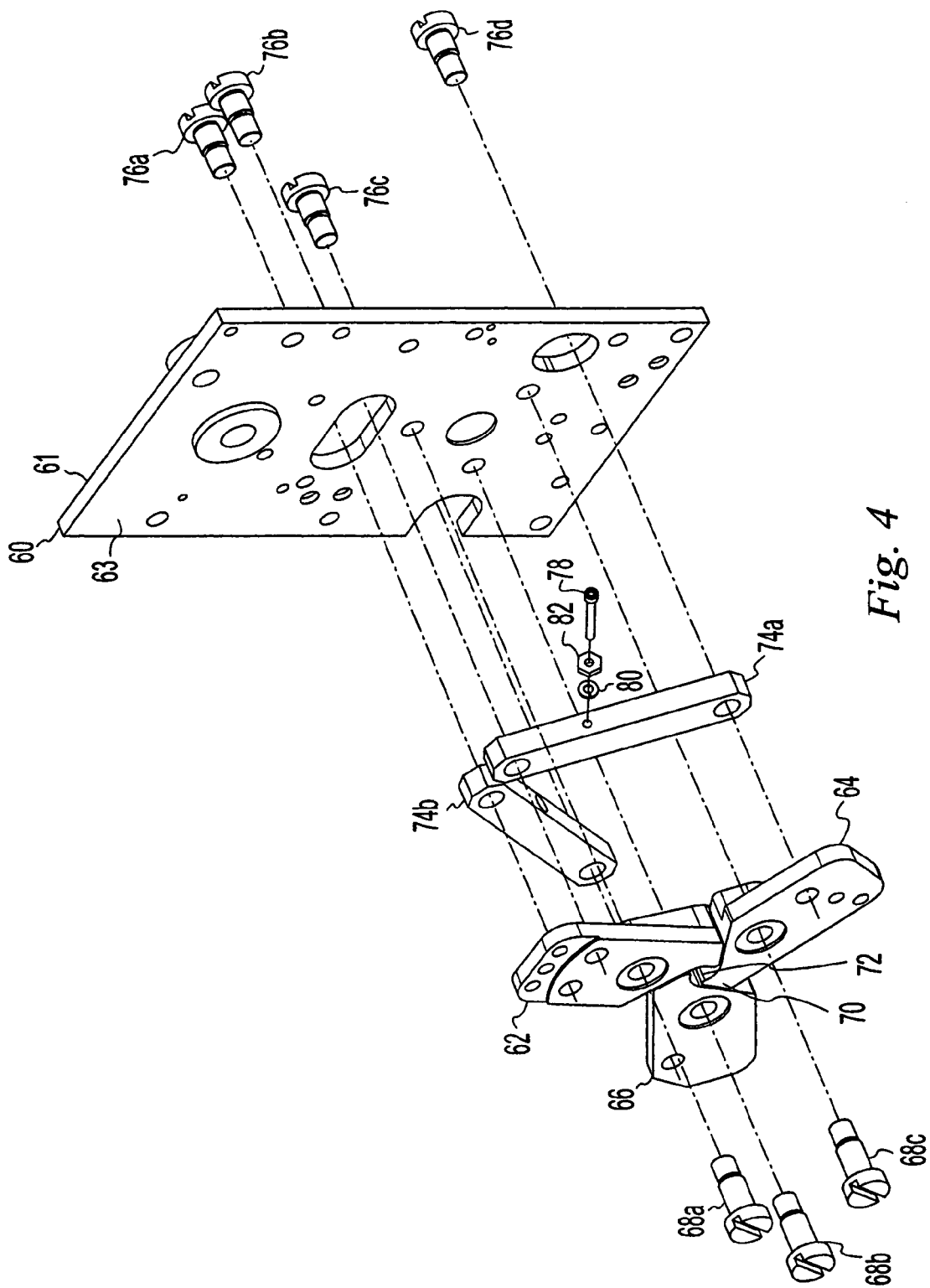
FIG. 4 is an exploded perspective view of the partially assembled light guide receptacle of FIG. 3.

Referring to FIG. 4, the illustrative light guide receptacle mechanism 44 includes a base plate 60 having a generally planar layout and including a plurality of mounting holes. The base plate 60 includes a front side 61 and a back side 63. A plurality of jaws is mounted to the base plate 60 for rotation relative to the base plate 60. The jaws include a first jaw 62, a second jaw 64, and a third jaw 66 each mounted with a jaw shoulder screw 68a-68c. The jaws 62, 64, 66 each include a radially inwardly projecting tab 70 with a transversely directed tooth 72. The tabs 70 and teeth 72 define the opening 16. As the jaws 62, 64, 66 rotate clockwise, the opening 16 enlarges. As the jaws 62, 64, 66 rotate counter clockwise, the opening 16 shrinks. The jaws 62, 64, 66 are connected to one another by a pair of links 74a, 74b and a plurality of link shoulder screws 76a-76d. One link 74a joins the first jaw 62 to the second jaw 64. The other link 74b joins the first jaw 62 to the third jaw 66. Thus, as the first jaw 62 pivots, it drives the second and third jaws 64, 66 via the links 74a, 74b to pivot in the same direction. A jaw switch actuator screw 78 threads into one of the links 74a and is secured by a lock washer 80 and nut 82.

Figure 5:
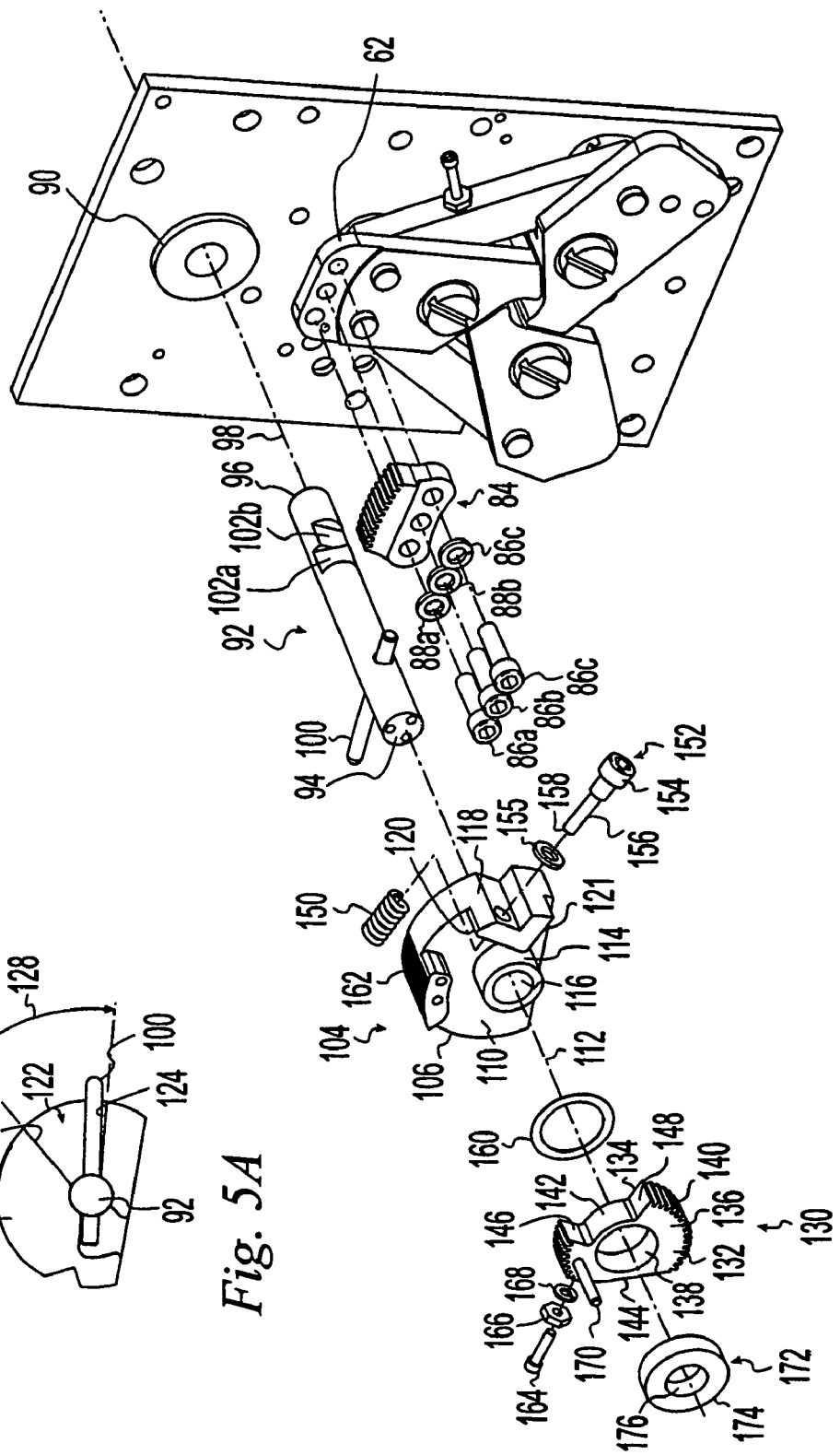
FIG. 5 is an exploded perspective view of the partially assembled light guide receptacle of FIG. 3.

Referring to FIG. 5, a jaw gear 84 is mounted to the first jaw 62 with a plurality of jaw gear screws 86a-c threaded into the first jaw 62 and secured with lock washers 88a-c. The jaw gear 84 provides an input mechanism for driving the jaws 62, 64, 66 to enlarge and shrink the opening 16. A bearing 90 extends through the base plate 60 and receives a drive shaft 92 for rotation. The drive shaft 92 includes an output end 94 projecting away from the back side 63 of the mounting plate 60, an input end 96 projecting from the front side of the plate 61, and an axis 98 extending between the output and input ends 94, 96. A dog pin 100 extends transversely through the drive shaft 92 near the output end 94. One or more flats 102a-102b are formed on the drive shaft 92 near the input end 96 to engage set screws for securing a handle described below.

A hub 104 includes a generally semi-cylindrical body 106 having a front side 108 (FIG. 5a), a back side 110, and an axis 112 extending therebetween. A boss 114 projects axially from the back side 110 and an axial through bore 116 extends through the boss 114 and hub body 106. A protrusion 118 projects rearwardly from the back side 110 and defines an upper shoulder 120 and a lower shoulder 121. The front side 108 (FIG. 5a) includes a relieved portion 122 formed into the hub 104. The relieved portion 122 is generally fan shaped and is defined at the extremes by a lower shoulder 124 and an upper shoulder 126 defining an angle 128 between them. The hub 104 is mounted to the drive shaft 92 for rotation with the output end 94 of the drive shaft 92 engaged with the through bore 116 of the hub 104. The relieved portion 122 receives the dog pin 100 and the drive shaft 92 and dog pin 100 are free to rotate counter clockwise through the angle 128 between the lower and upper shoulders 124, 126 before the dog pin 100 engages the upper shoulder 126 and begins to drive the hub 104.

A hub gear 130 includes a generally disk shaped body 132 having a front face 134, a back face 136, and an axial through bore 138 extending between the front and back faces 134, 136. The body 132 includes gear teeth 140 formed circumferentially over a portion of the outer diameter of the body 132. The body 132 further includes first and second cutouts 142, 144. The angular limits of the first cutout 142 are defined by upper and lower surfaces 146, 148. The hub gear 130 is mounted to the boss 114 of the hub 104 for rotation. The boss 114 is received in the through bore 138 of the hub gear 130. A lock spring 150 is interposed between the upper surface 146 of the first hub gear cutout 142 and the upper shoulder 120 of the hub protrusion 118 to bias the hub 104 and hub gear 130 angularly so that the lower surface 148 of the first cutout 142 abuts the lower shoulder 121 of the protrusion 118 on the hub. A lock spring 150 biases the hub gear 130 and hub 104 to rotate together. A lock spring screw 152 includes a head 154, a shaft 156, and a tip 158. The lock spring screw 152 is threaded through the protrusion 118 and is secured by a washer 155 trapped between the head 154 and protrusion 118. The lock spring screw 152 extends through the protrusion 118 and the shaft 156 is positioned inside of the lock spring 150 to retain the lock spring 150. The lower surface 148 of the first cutout 142 of the hub gear 130 abuts the lower shoulder 121 of the hub protrusion 118 to limit the clockwise rotation of the hub gear 130 relative to the hub 104. The upper surface 146 abuts the lock spring 150 and counterclockwise rotation may be limited by the compressed height of the lock spring 150. Alternatively, the upper surface 146 may abut the tip 158 to limit counterclockwise rotation of the hub gear 130 relative to the hub 104 such that the length of the shaft 156 determines the amount of counterclockwise rotation.

A washer 160 is interposed between the hub 104 and hub gear 130 to reduce friction and facilitate relative rotation. Ratchet teeth 162 are formed on a portion of the outer diameter of the hub 104 and define part of a lock mechanism described below. A hub gear spring screw 164 threads into the hub gear 130 and is secured by a nut 166 and lock washer 168. The hub gear spring screw 164 defines an attachment point for a spring described below. A lock switch pin 170 projects from the back 136 face of the hub gear 130 to actuate a switch described below. A spacer 172 includes a cylindrical body 174 and an axial through bore 176 that receives the output end 94 of the drive shaft 92 and provides an enlarged support surface surrounding the drive shaft 92.

Figure 6:
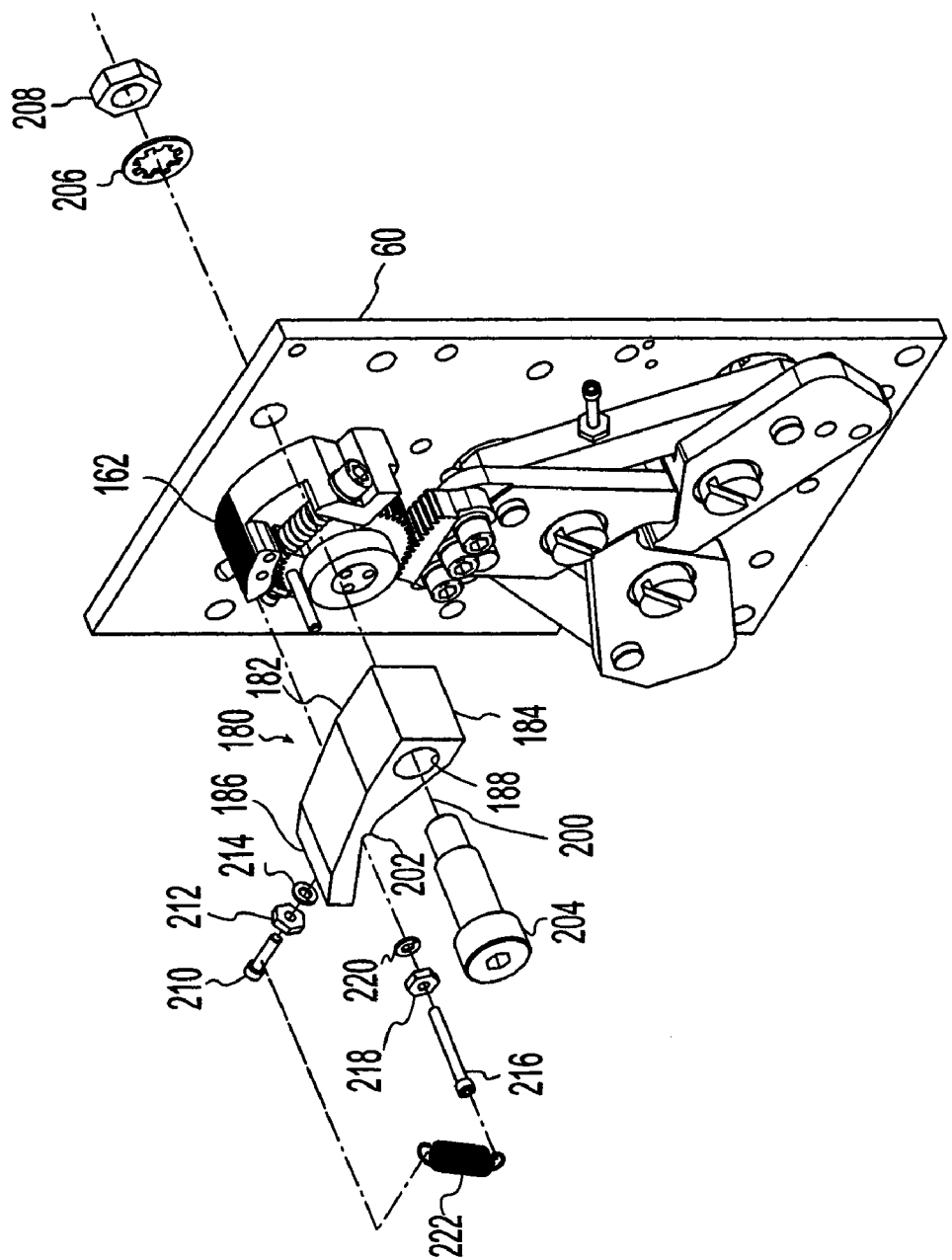
FIG. 6 is an exploded perspective view of the partially assembled light guide receptacle of FIG. 3.

Referring to FIG. 6, a pawl 180 includes a body 182 having a pivot end 184 and a free end 186. The pivot end 184 includes a pivot hole 188 defining a pivot axis 200. A tooth 202 projects downwardly intermediate the pivot and free ends 184, 186 for engaging the ratchet teeth 162 of the hub 104. The pawl 180 is mounted to the base plate 60 for rotation with a pawl shoulder screw 204 inserted through the pivot hole 188 and threaded through the plate 60 and secured with a lock washer 206 and nut 208. A pawl spring screw 210 is threaded into the free end 186 and secured with a nut 212 and lock washer 214 to provide an attachment point. A pawl spring/plate screw 216 is threaded into the base plate 60 and secured with a nut 218 and lock washer 220 to provide another attachment point. A pawl spring 222 is stretched between the pawl spring screw 210 and pawl spring/plate screw 216 with an end looped over each screw to bias the pawl 180 downwardly and engage the tooth 202 with the ratchet teeth 162 of the hub 104.

Figure 7:
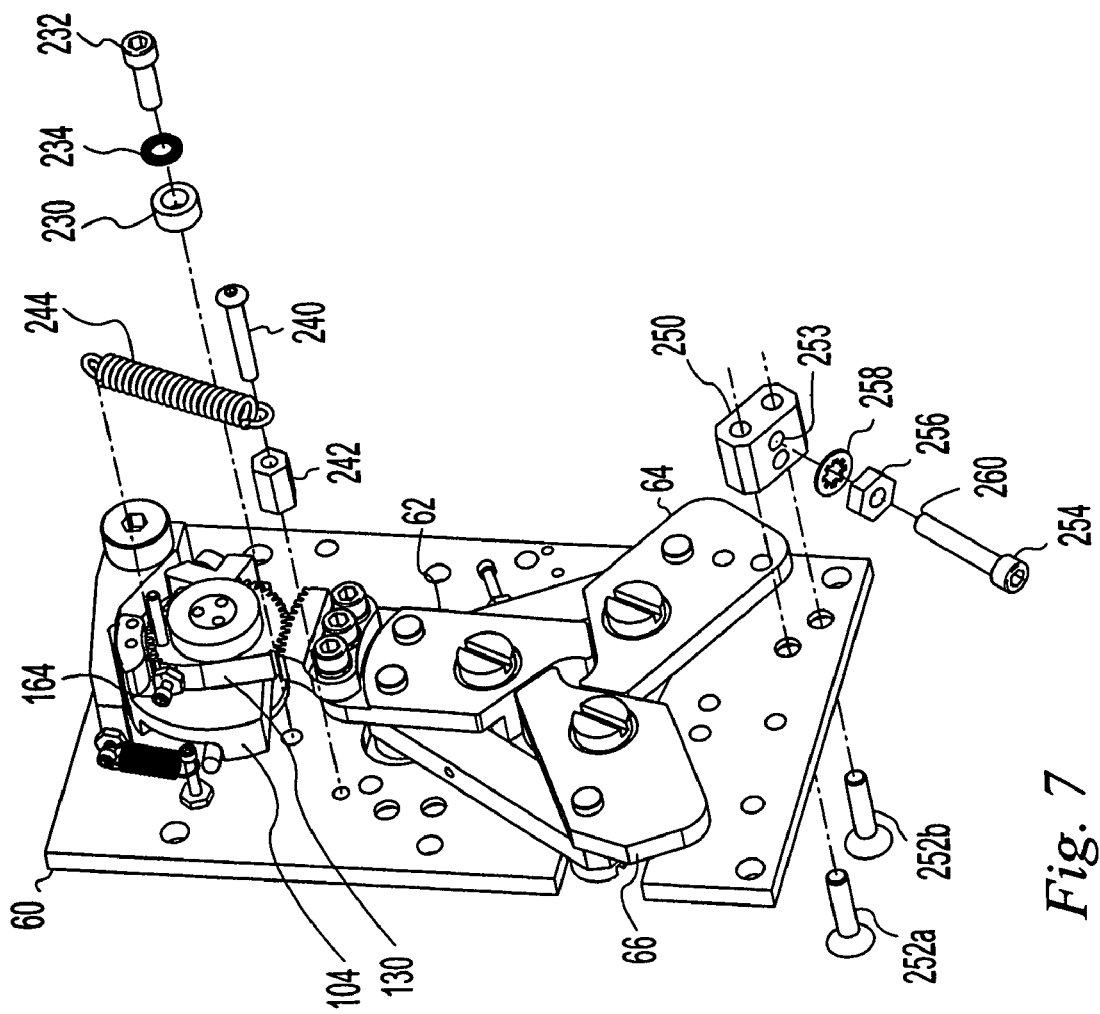
FIG. 7 is an exploded perspective view of the partially assembled light guide receptacle of FIG. 3.

Referring to FIG. 7, a hub stop spacer 230 is mounted to the base plate 60 below the hub 104 with a hub stop spacer screw 232 and a lock washer 234. The hub 104 abuts the hub stop spacer 230 to limit clockwise rotation of the hub 104 relative to the base plate 60. A hub gear/plate spring screw 240 and hub gear spring standoff 242 are mounted to the base plate 60 to provide an attachment point. A hub gear spring 244 is stretched between the hub gear spring screw 164 and hub gear/plate spring screw 240 to bias the hub gear 130 clockwise and thus bias the jaws 62, 64, 66 toward the closed position. A second jaw stop block 250 is mounted to the base plate 60 with second jaw stop block screws 252a-b inserted through the plate from the front side and threaded into the second jaw stop block 250. The second jaw stop block 250 includes a threaded through hole 253 aligned with the second jaw 64. A second jaw stop block adjusting screw 254 is threaded into the hole 253 and secured with a nut 256 and lock washer 258. The tip 260 of the screw 254 abuts the second jaw 64 to limit counter clockwise rotation of the jaws 62, 64, 66 and thus establish the minimum size for the opening 16. By advancing or retracting the second jaw stop block adjusting screw 254 the minimum opening size can be adjusted. For example, the minimum opening size can be adjusted to prevent the tabs 70 and teeth 72 of the jaws 62, 64, 66 from colliding with one another.

Figure 8:
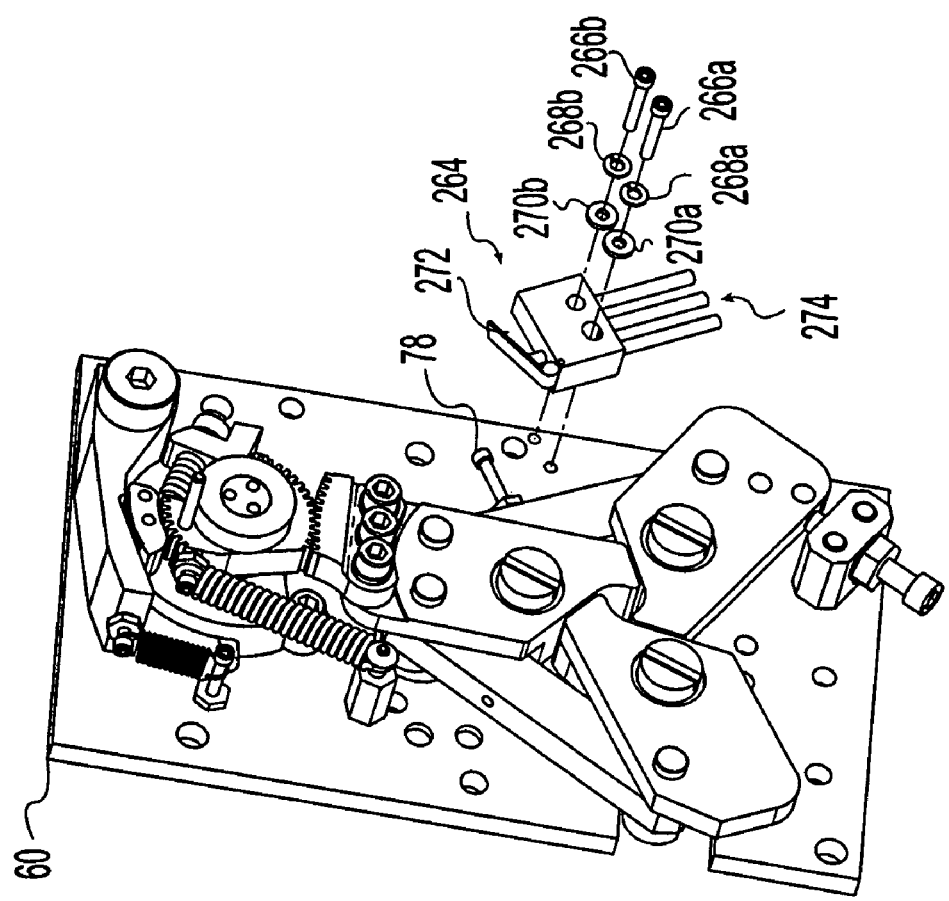
FIG. 8 is an exploded perspective view of the partially assembled light guide receptacle of FIG. 3.

Referring to FIG. 8, a jaw switch 264 is mounted to the plate with jaw switch screws 266a-b, lock washers 268a-b, and flat washers 270a-b. The jaw switch 264 includes a treadle 272 operable to open and close electrical contacts within the switch and a wiring harness 274 extending from the electrical contacts to provide switching at a remote location. The jaw switch 264 is mounted with the treadle 272 below and adjacent to the jaw switch actuator screw 78 so that as the jaws 62, 64, 66 and links 74a-b move, the jaw switch actuator screw 78 operates the switch. In the illustrative arrangement, the jaw switch actuator screw 78 moves away from the jaw switch 264 as the jaws 62, 64, 66 open and moves toward the jaw switch 264 as the jaws 62, 64, 66 close.

Figure 9:
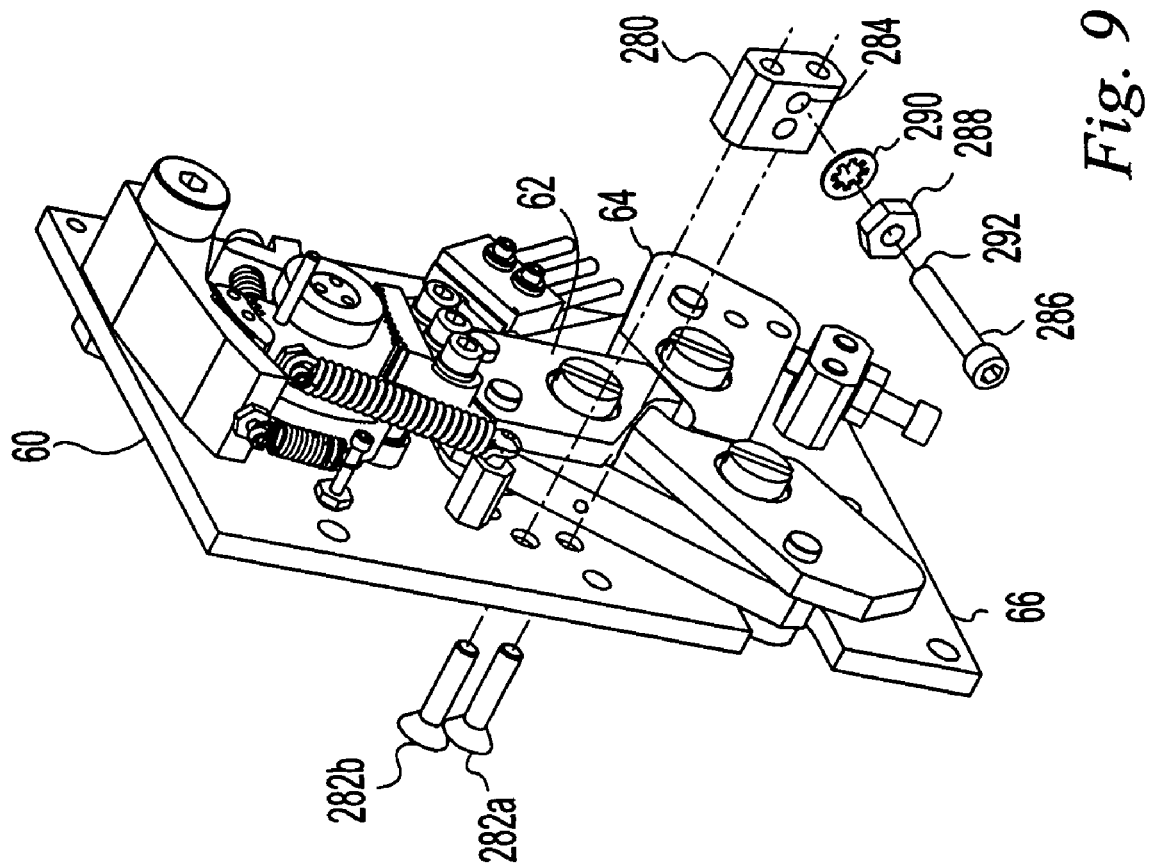
FIG. 9 is an exploded perspective view of the partially assembled light guide receptacle of FIG. 3.

Referring to FIG. 9, a first jaw stop block 280 is mounted to the base plate 60 with first jaw stop block screws 282a-b inserted through the base plate 60 from the front side and threaded into the first jaw stop block 280. The first jaw stop block 280 includes a threaded through hole 284 aligned with the first jaw 62. A first jaw stop block adjusting screw 286 is threaded into the hole 284 and secured with a nut 288 and lock washer 290. The tip 292 of the screw 286 abuts the first jaw 62 to limit clockwise rotation of the jaws 62, 64, 66 and thus establish the maximum size for the opening 16. By advancing or retracting the first jaw stop block adjusting screw 286 the maximum opening size can be adjusted.

The operation of the jaw mechanism will be explained with reference to FIGS. 10 and 11. FIG. 10 is a front plan view of the partially assembled light guide receptacle at the same stage of assembly as depicted in FIG. 9 with a portion of the mounting plate cut away to better reveal the mechanism. FIG. 11 is a back plan view of the partially assembled light guide receptacle at the same stage of assembly as depicted in FIG. 9. As the drive shaft 92 is rotated counter clockwise, the dog pin 100 rotates up away from lower shoulder 124 of the relieved portion 122 of the hub 104. As the dog pin 100 nears the upper shoulder 126, it contacts the lower side of the pawl 180 and raises the pawl 180 against pawl spring 222 tension to disengage the pawl tooth 202 from the ratchet teeth 162 of the hub 104. This is shown in detail in FIG. 11a. This frees the hub 104 and allows it to rotate with the drive shaft 92 and dog pin 100 as the dog pin 100 is rotated against the upper shoulder 126 of the relieved portion 122 of the hub 104. The lower shoulder 121 of the protrusion 118 on the rear of the hub 104 abuts the lower surface 148 of the first cutout 142 of the hub gear 130 (FIG. 11) and drives the hub gear 130 counter clockwise. Continued counter clockwise rotation of the drive shaft extends the hub gear spring 244 and drives the jaw gear 84 clockwise causing the jaws 62, 64, 66 to pivot clockwise about the jaw shoulder screws 68a-c. Thus, rotating the drive shaft 92 counter clockwise opens the jaws 62, 64, 66 to expand the opening 16 to receive a light guide 18. The jaw motion, and consequently the opening 16 size, is limited by abutment of the first jaw 62 with the tip 292 of the first jaw stop block adjustment screw 286. A light guide 18 is inserted into the opening 16 and the mechanism is allowed to return toward its rest position under the influence of the hub gear spring 244. The hub gear spring 244 biases the hub gear 130 and jaw gear 84 clockwise to clamp the jaws around the light guide 18.

The jaws 62, 64, 66 and links 74a-b provide a 3:1 mechanical advantage. The hub gear spring 244 driving the 3:1 mechanical advantage produces a tight grip on the light guide 18. However, for additional retention force, the drive shaft 92 may be rotated clockwise to move the hub 104 into a locked position. The dog pin 100 pushes on the lower shoulder 124 of the relieved portion 122 of the hub 104 and rotates the hub 104 clockwise. The lower shoulder 121 of the protrusion 118 moves away from the lower surface 148 of the first cutout 142 of the hub gear 130 and the lock spring 150 is compressed between the upper shoulder 120 of the hub protrusion 118 and the upper surface 146 of the first hub gear cutout 142. The pawl tooth 202 engages the ratchet teeth 162 of the hub 104 to hold the lock spring 150 in the compressed condition. The increased force generated by the compressed lock spring 150 increases the retention force with which the jaws 62, 64, 66 grip the light guide 18. To release the light guide 18, the drive shaft 92 is rotated counter clockwise until the dog pin 100 again raises the pawl 180 to disengage the pawl tooth 202 from the ratchet teeth 162 of the hub 104 and releases the lock spring 150 back to its rest condition. Continued counter clockwise rotation of the drive shaft 92 opens the jaws 62, 64, 66 as previously described so that the light guide 18 can be removed.

Figure 12:
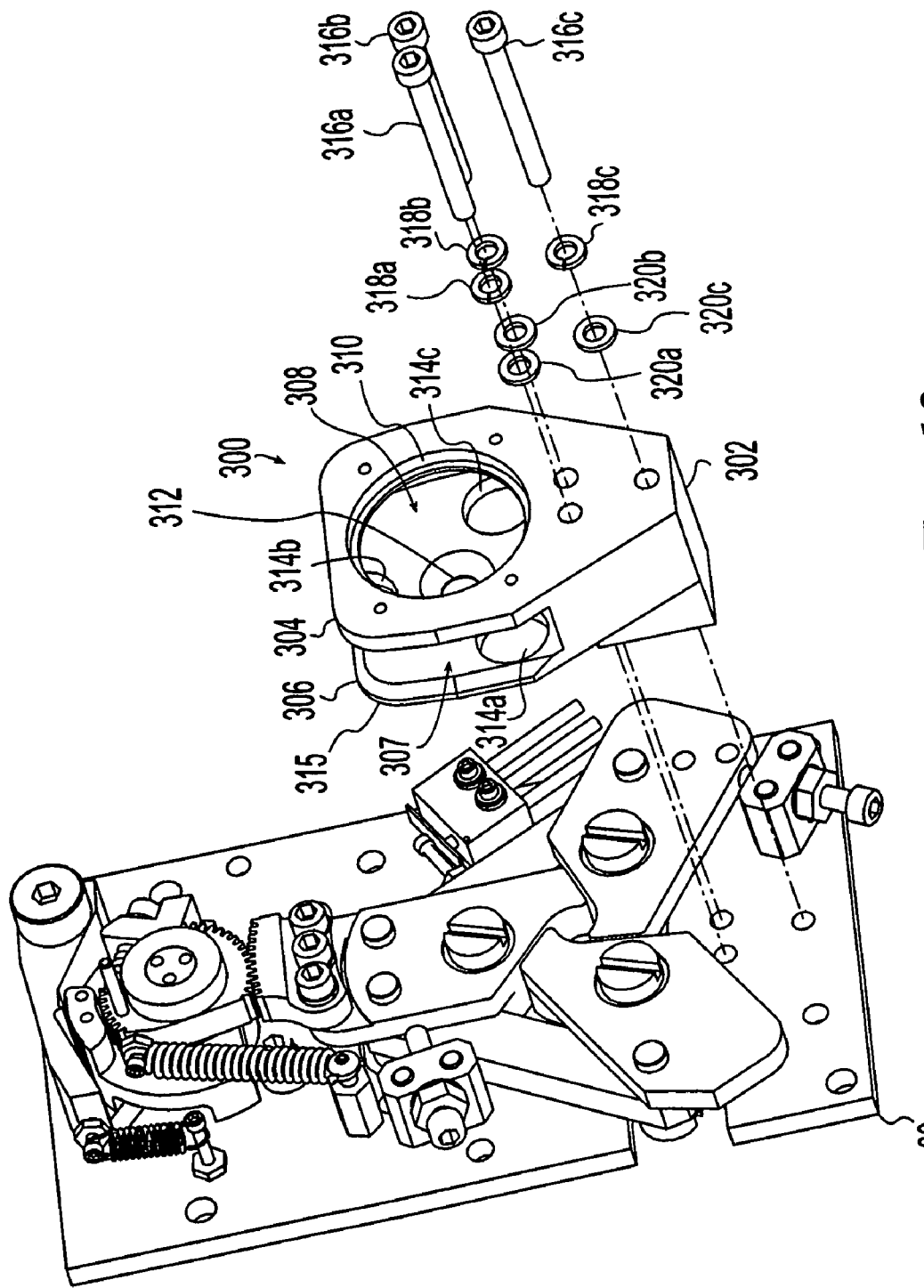
FIG. 12 is an exploded perspective view of the partially assembled light guide receptacle of FIG. 3.

Referring to FIG. 12, a stop plate 300 includes a body 302 having back and front cantilevered shelves 304, 306 defining an open space 307 between them. The back shelf 304 includes a central opening 308 having a countersunk rim 310 defining a lens holder. The front shelf 306 includes a central aperture 312 through which light passes to reach the opening 16 and the light guide 18. The front shelf 306 further includes three through holes 314a-c for providing clearance for the heads of the jaw shoulder screws 68a-c. The front shelf 306 of the stop plate 300 provides a front surface 315 surrounding the aperture 312 against which the light guide 18 may abut to set the depth of the light guide 18 relative to the light guide receptacle. The stop plate 300 is mounted to the base plate 60 with stop plate screws 316a-c extended through the stop plate 300 and threaded into the base plate 60. The stop plate screws 316*a-c* are secured with lock washers 318*a-c* and flat washers 320*a-c*.

Figure 13:
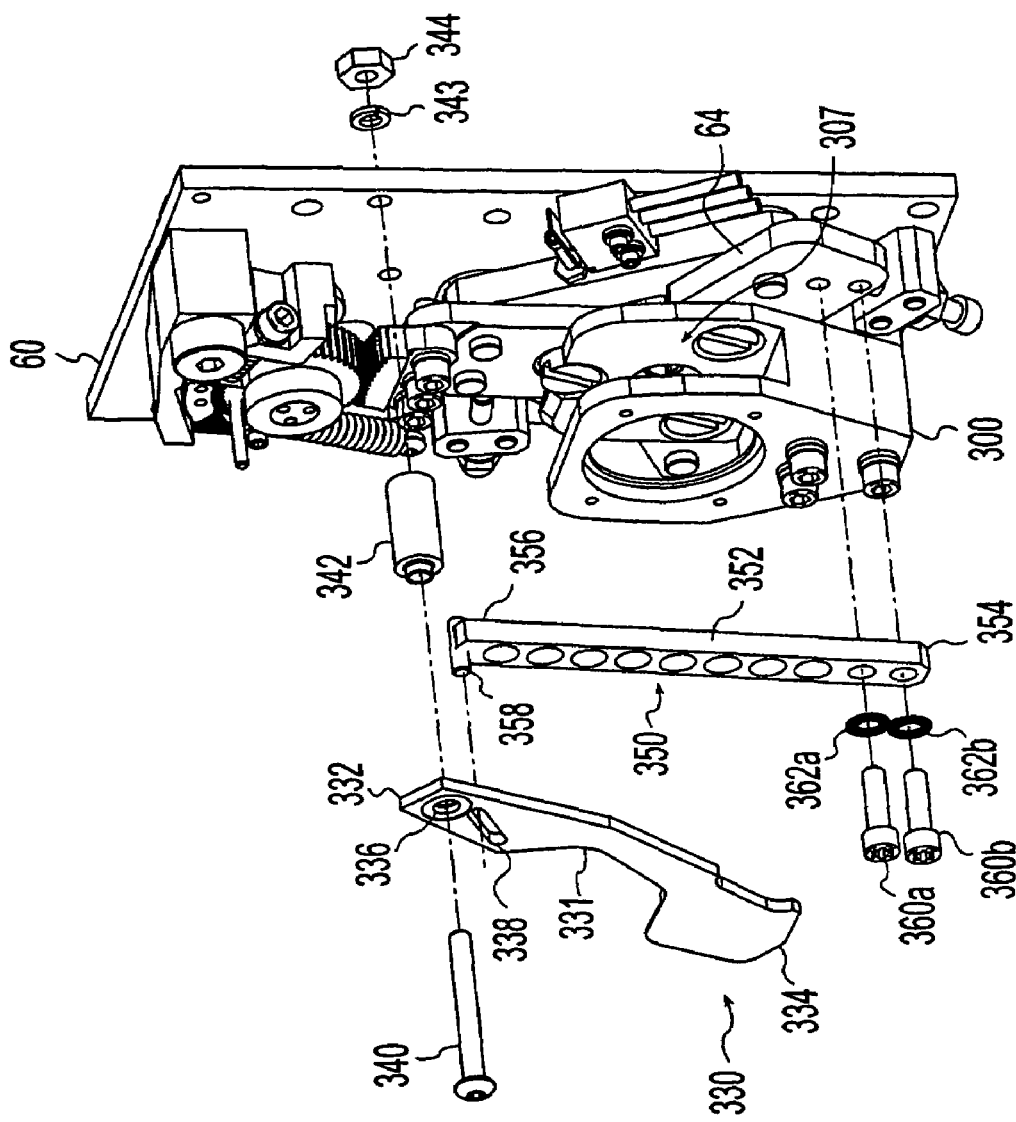
FIG. 13 is an exploded perspective view of the partially assembled light guide receptacle of FIG. 3.

Referring to FIG. 13, a first shield 330 is provided to prevent accidental exposure of a user to light from the light source 10. The first shield 330 includes an elongated planar body 331 having a pivot end 332 and an enlarged light blocking end 334. The pivot end 332 includes a pivot hole 336 and a pin follower slot 338. The first shield 330 is mounted to the base plate 60 for rotation by a first shield screw 340 extended through the pivot hole 336, through a first shield standoff 342, and through the base plate 60. The first shield screw 340 is secured by a lock washer 343 and nut 344. The first shield standoff 342 spaces the first shield 330 from the base plate 60 so that the first shield 330 clears the other elements mounted to the base plate 60 and can swing through the open space 307 defined by the front and back shelves 304, 306 of the stop plate 300. An arm 350 includes an elongated body 352 having a mounting end 354 and an output end 356. The output end 356 includes a pin 358. The arm 350 is mounted to the second jaw 64 by arm screws 360*a-b* extended through the mounting end 354 and threaded into the second jaw 64. The arm screws 360*a-b* are secured by lock washers 362*a-b*. The pin 358 at the output end 356 of the arm 350 is engaged with the pin follower slot 338. As the second jaw 64 rotates, the arm 350 rotates with it. The pin follower slot 338 follows the pin 358 causing the first shield 330 to pivot about the first shield screw 340 and standoff 342.

Figure 14:
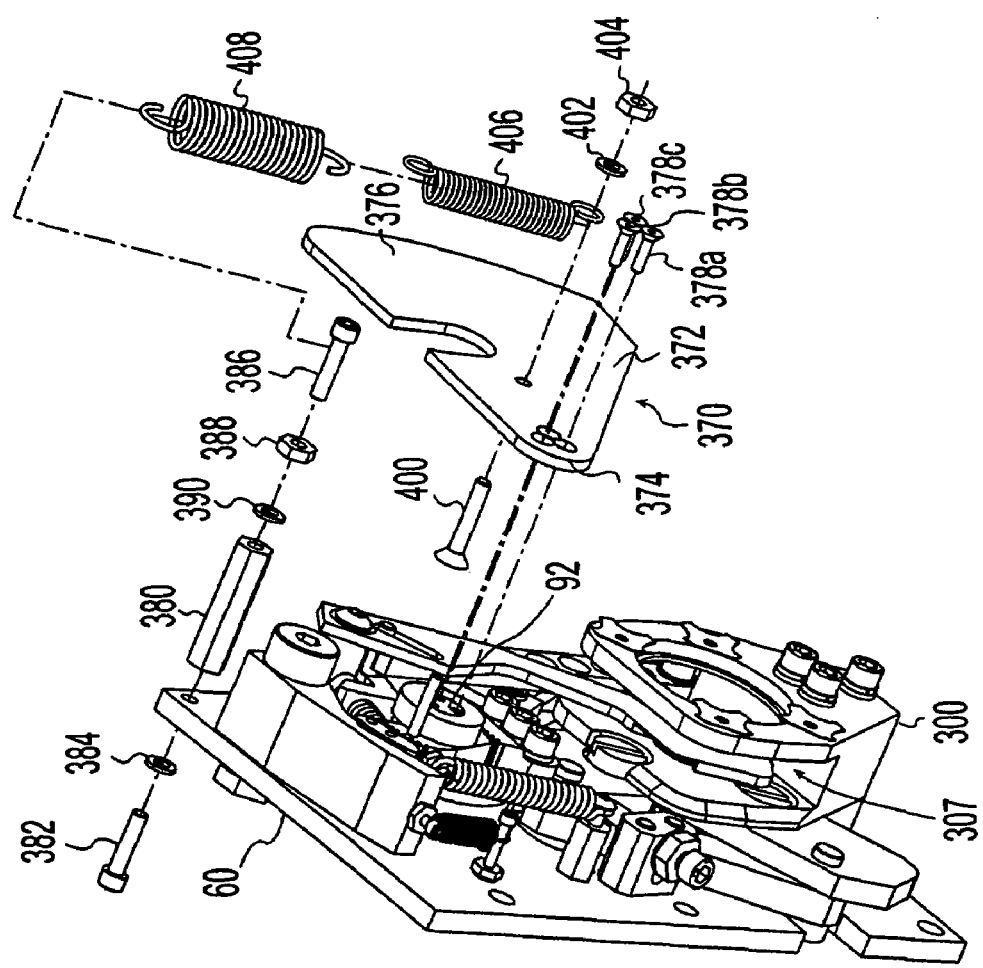
FIG. 14 is an exploded perspective view of the partially assembled light guide receptacle of FIG. 3.

Referring to FIG. 14, a second shield 370 is provided to prevent accidental exposure of a user to light from the light source 10. The second shield 370 includes an elongated planar body 372 having a pivot end 374 and an enlarged light blocking end 376. The second shield 370 is mounted to the drive shaft 92 in fixed angular relationship for rotation with the drive shaft 92 by second shield screws 378*a-c* extended through the second shield and threaded into the output end 94 of the drive shaft 92. The drive shaft 92 spaces the second shield 370 from the base plate 60 so that the second shield 370 clears the other elements mounted to the base plate 60 and can swing through the open space 307 defined by the front and back shelves 304, 306 of the stop plate 300. A second shield spring standoff 380 is mounted to the base plate 60 by a second shield spring standoff mounting screw 382 extended through the base plate 60 and threaded into the second shield spring standoff 380 and secured by a lock washer 384. A second shield standoff spring screw 386 is threaded into the second shield spring standoff 380 from the back and is secured by a nut 388 and lock washer 390 to provide an attachment point. A second shield spring screw 400 is mounted to the second shield 370 by being extended through the second shield and secured by a lock washer 402 and nut 404 to provide another attachment point. Inner and outer second shield springs 406, 408 are coaxially mounted with an end looped over each of the second shield spring standoff screw 386 and second shield spring screw 400. The springs bias the second shield, and consequently the drive shaft, clockwise toward their rest positions.

Figure 15:
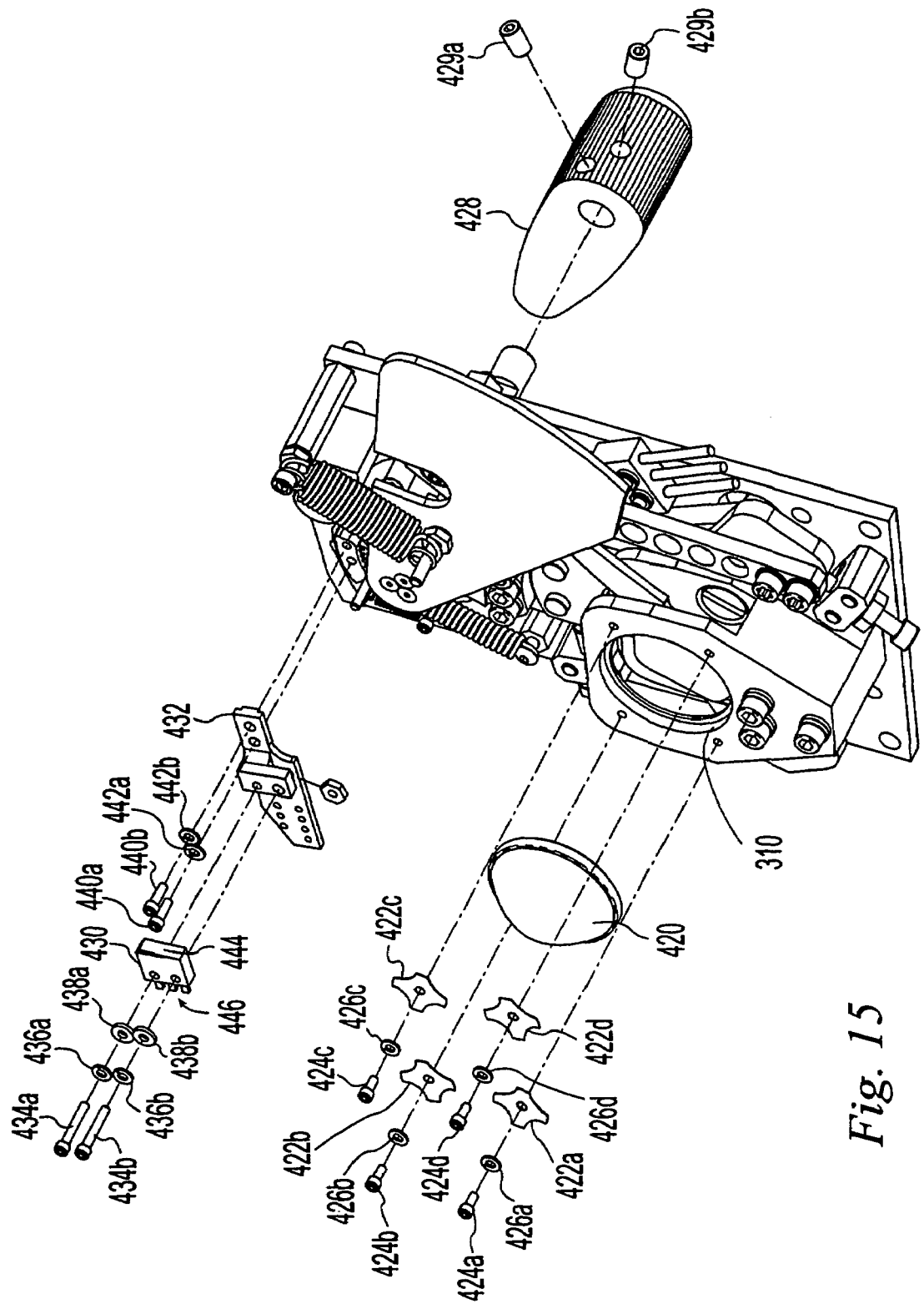
FIG. 15 is an exploded perspective view of the partially assembled light guide receptacle of FIG. 3.

Referring to FIG. 15, a lens 420 is seated in the countersunk rim 310 of the back shelf 304 of the stop plate 300. The lens 420 is retained by lens retaining springs 422*a-d* held in place by lens screws 424*a-d* extended through the lens retaining springs 422*a-d*, threaded into the stop plate 300, and secured by lock washers 426*a-d*. The lens 420 focuses light into the light guide 18. An actuator knob 428 is mounted to the input end 96 of the drive shaft 92 by set screws 429*a-b* to provide a grip for a user to rotate the drive shaft 92 in use. A lock switch 430 is provided to indicate when the locking feature of the mechanism is engaged. The lock switch 430 is mounted to a lock switch mount 432 by lock switch screws 434*a-b* extended through the lock switch 430, threaded into the lock switch mount 432, and secured by lock washers 436*a-b* and flat washers 438*a-b*. The lock switch mount 432 is mounted to the hub 104 by lock switch mount screws 440*a-b* extended through the lock switch mount 432, threaded into the hub 104, and secured with lock washers 442*a-b*. The lock switch 430 includes a treadle 444 operable to open and close electrical contacts within the switch and a wiring harness 446 extending from the electrical contacts to provide switching at a remote location.

Figure 16:
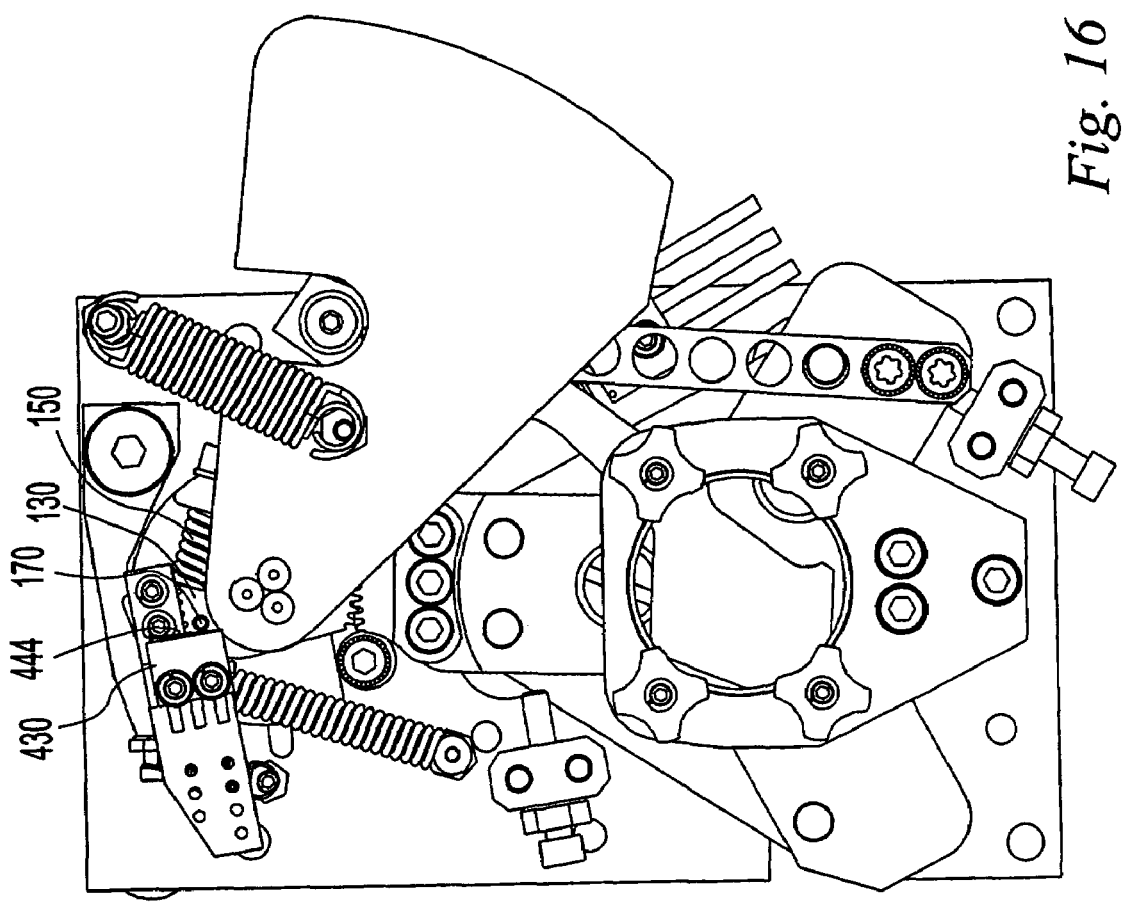
FIG. 16 is a plan view of the fully assembled light guide receptacle of FIG. 3.

Referring to FIG. 16, the lock switch 430 is positioned with the treadle 444 adjacent the lock switch pin 170 projecting from the hub gear 130. The lock switch pin 170 actuates the lock switch as the hub 104 is moved between the unlocked position in which the lock spring 150 is in its rest position and the locked position in which the lock spring 150 is further compressed. In the illustrative arrangement, the hub 104 and lock switch are rotated clockwise relative to the hub gear 130 in the locked position such that the lock switch pin 170 is nearer the lock switch 430 in the unlocked position and the lock switch pin 170 is further from the lock switch 430 in the locked position.

FIGS. 17-28 illustrate the light guide receptacle mechanism 44 in different states of operation. The actuator knob 428, set screws 42*a-b*, bearing 90, and mounting plate 60 have been omitted from the drawings to aid visualization. FIGS. 17, 19, 21, 23, 25, and 27 show the light guide receptacle 14 from the front while FIGS. 18, 20, 22, 24, 26, and 28 show it from the back in corresponding states of operation.

Referring to FIGS. 17 and 18, the light guide receptacle mechanism 44 is shown in the rest, or closed, state. The second jaw 64 abuts the second jaw stop block adjusting screw 254 limiting counter clockwise rotation of the jaws 62, 64, 66 and thus the minimum opening 16 size. The jaw switch 264 and lock switch 430 are depressed. The first shield 330 blocks the opening 16 to prevent light from exiting the opening 16. The pin 358 on the arm 350 is near the end of the pin follower slot 338 nearest the pivot end 332 of the first shield 330. The second shield 370 is pivoted clockwise by the inner and outer second shield springs 406, 408 to its rest position. The drive shaft 92 moves with the second shield 370 and drives the dog pin 100, hub 104, and hub gear 130 clockwise to rotate the gears 62, 64, 66 to the closed position. The pawl spring 222 biases the pawl 180 into engagement with the ratchet teeth 162 of the hub 104 to prevent the hub 104 from rotating counterclockwise.

Figure 20:
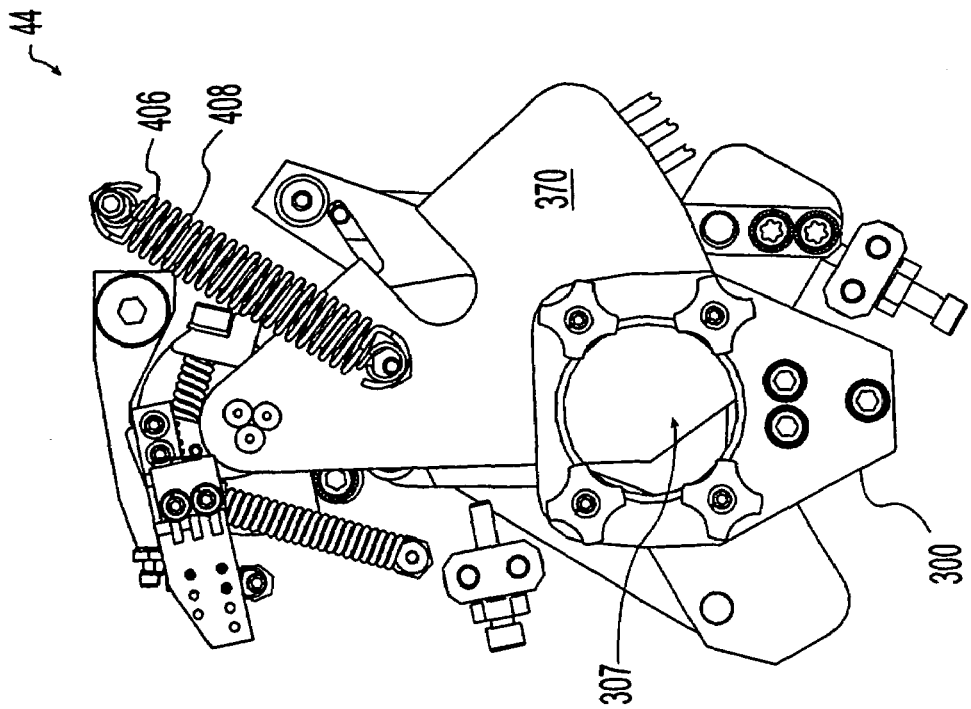
FIG. 20 is a back plan view of the fully assembled light guide receptacle of FIG. 3 in the same operating position as FIG. 19.
Figure 19:
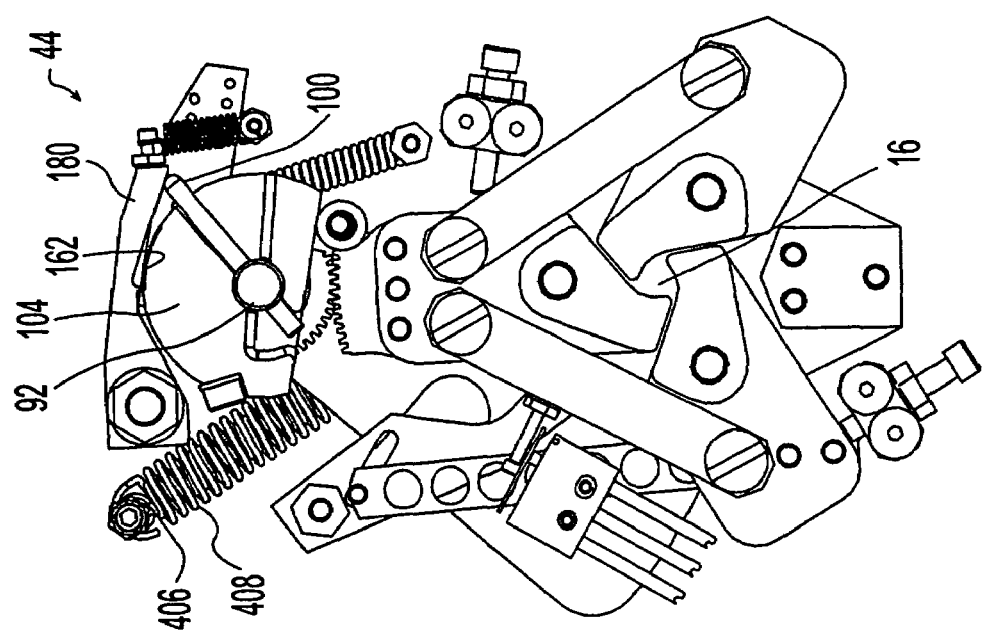
FIG. 19 is a front plan view of the fully assembled light guide receptacle of FIG. 3 (with certain elements omitted to aid visualization) in one operating position.

Referring to FIGS. 19 and 20, the actuator knob (not shown) has been rotated counterclockwise to rotate the drive shaft 92, dog pin 100, and second shield 370 clockwise while stretching the inner and outer second shield springs 406, 408. The second shield 370 has rotated into the open space 307 defined by the stop plate 300 so that it also now blocks light from exiting the opening 16. The dog pin 100 abuts the pawl 180 and has just raised it to disengage the pawl 180 from the ratchet teeth 162. The dog pin 100 has not yet engaged the hub 104 and none of the rest of the mechanism has moved.

Figure 22:
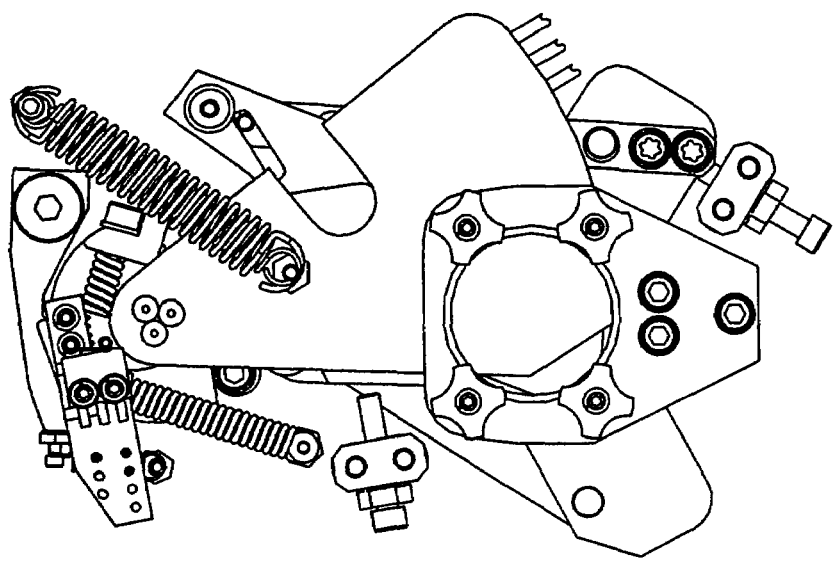
FIG. 22 is a back plan view of the fully assembled light guide receptacle of FIG. 3 in the same operating position as FIG. 21.
Figure 21:
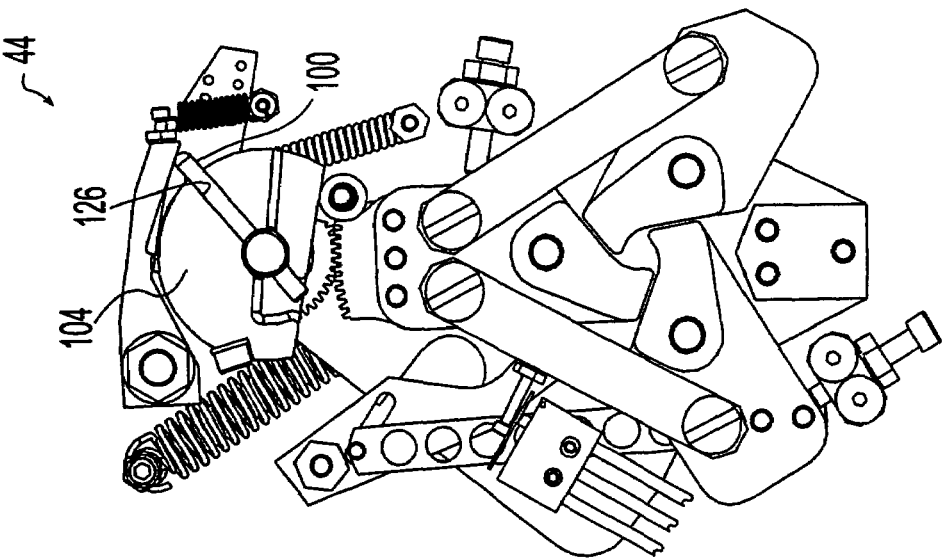
FIG. 21 is a front plan view of the fully assembled light guide receptacle of FIG. 3 (with certain elements omitted to aid visualization) in one operating position.

Referring to FIGS. 21 and 22, the actuator knob has been rotated slightly further counter clockwise so that the dog pin 100 now engages the upper shoulder 126 of the hub 104 and any further counter clockwise rotation will cause the hub 104 to rotate and drive the mechanism toward the open position.

Figure 24:
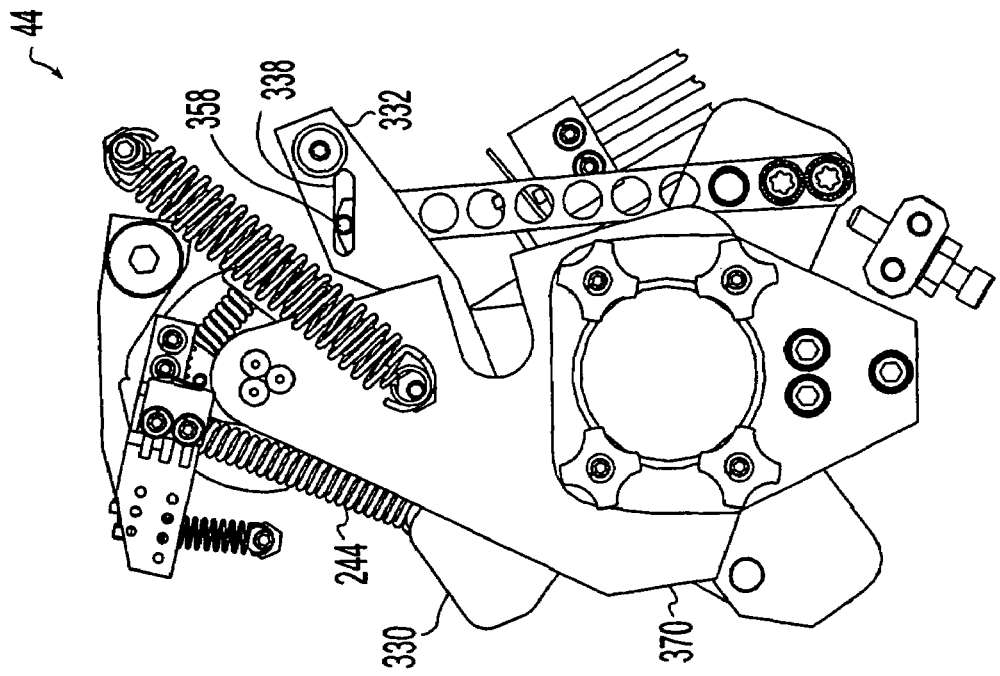
FIG. 24 is a back plan view of the fully assembled light guide receptacle of FIG. 3 in the same operating position as FIG. 23.
Figure 23:
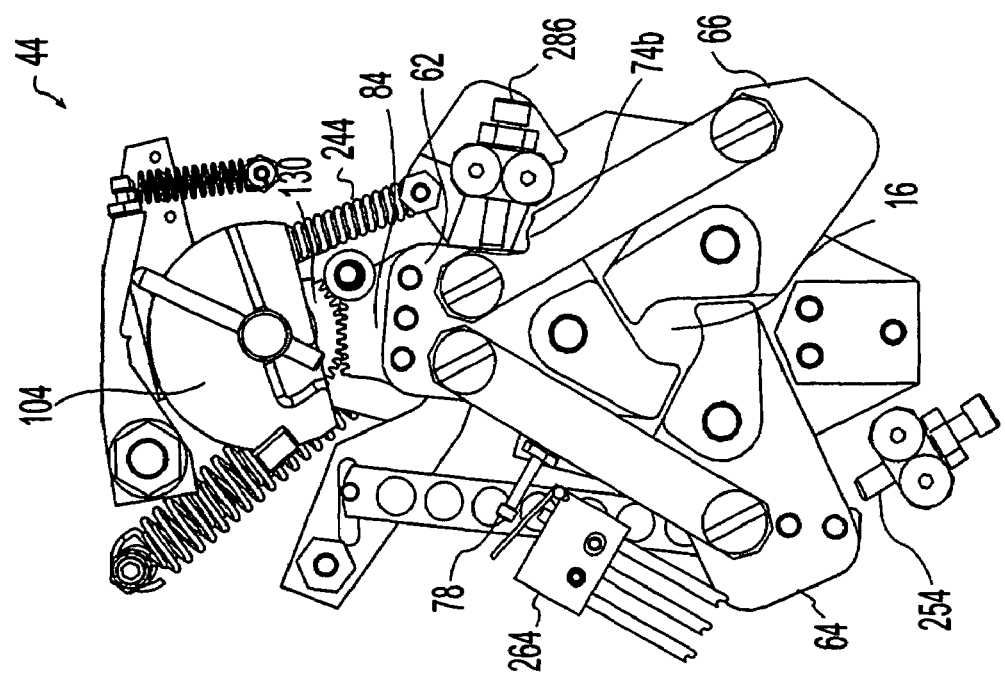
FIG. 23 is a front plan view of the fully assembled light guide receptacle of FIG. 3 (with certain elements omitted to aid visualization) in one operating position.

Referring to FIGS. 23 and 24, the actuator knob has been rotated counter clockwise to the fully open position. The second shield springs 406, 408 have been stretched further and the hub gear spring 244 has been stretched. The hub 104, hub gear 130, jaw gear 84, and jaws 62, 64, 66 have all rotated until the first jaw 62 abuts the first jaw stop block adjustment screw 286 thus limiting the maximum opening 16 size. A portion of link 74b is shown cut away so that the abutment of the first jaw 62 with the first stop block adjustment screw 286 can be seen. The first shield 330 has moved completely through the open space 307 and the second shield 370 blocks light from the opening 16. The arm pin 358 engages the pin follower slot 338 near the pivot end 332 of the first shield 330 such that the first shield is very responsive to initial pin 358 movement. The first shield 330 rotates to the full open position within the first few degrees of jaw rotation. Continued jaw rotation causes little movement of the first shield 330 as the pin 358 moves in the pin follower slot 338 further from the pivot end 332 in a relatively unresponsive portion of the pin 358 and pin follower slot 338 engagement.

Still referring to FIGS. 23 and 24, the jaw switch 264 is no longer depressed as the jaw switch actuator screw 78 rotates away from the jaw switch 264. The jaw switch actuator screw 78 actuates the jaw switch 264 during the first few degrees of jaw rotation such that the jaw switch 264 acts quickly to indicate jaw motion. The jaw switch may be connected to the rest of the light source 10 to control a light source 10 function upon jaw movement. For example, the jaw switch 264 may trigger the power supply 38, light producing element 40, shutter 50, and/or some other light source 10 function. The jaw switch 264 may be connected directly to any light source 10 function to switch the function directly. Alternatively, the jaw switch 264 may be connected to a controller 52 to trigger a state within the controller 52 logic. The controller may then execute an instruction and control a function based on the jaw switch 264 position. For example, in one embodiment, the controller 52 may respond to operation of the jaw switch 264 to open the shutter 50 to allow light into the lens 42.

Figure 25:
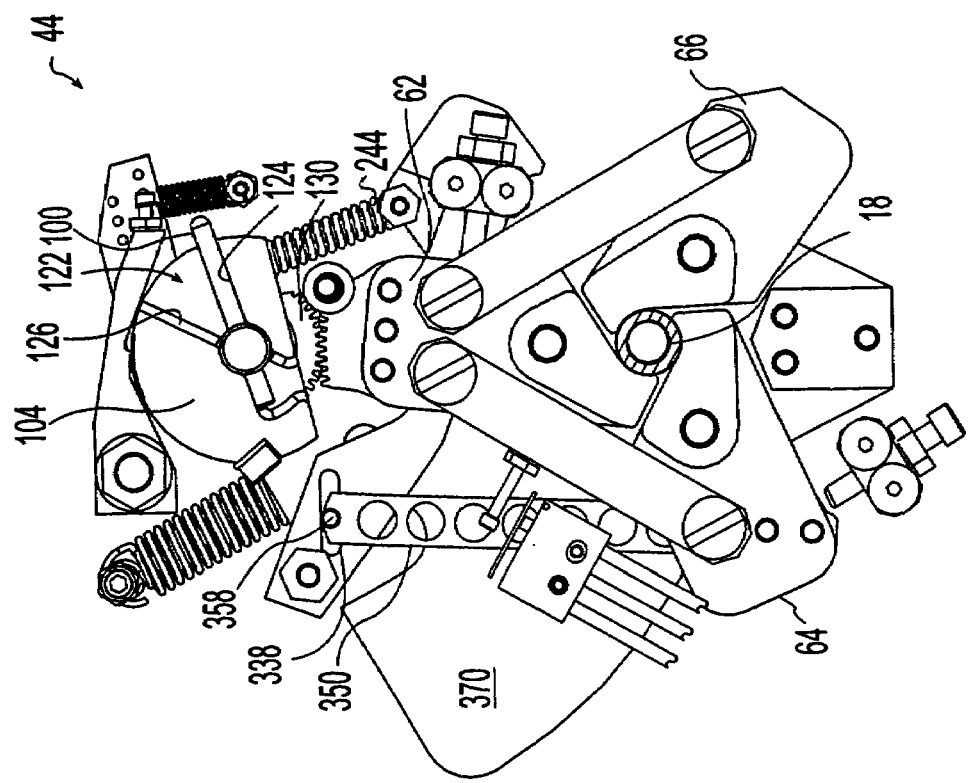
FIG. 25 is a front plan view of the fully assembled light guide receptacle of FIG. 3 (with certain elements omitted to aid visualization) in one operating position.
Figure 26:
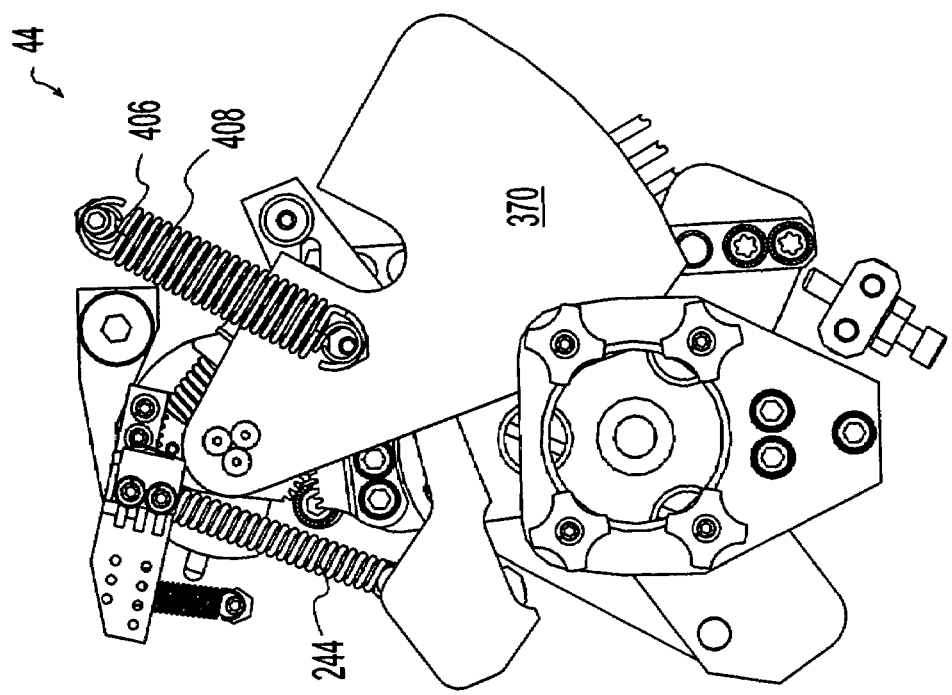
FIG. 26 is a back plan view of the fully assembled light guide receptacle of FIG. 3 in the same operating position as FIG. 25.

Referring to FIGS. 25 and 26, a light guide 18 has been inserted into the opening 16 and the actuator knob has been released to allow the jaws 62, 64, 66 to close under spring pressure and grip the light guide 18. The hub gear spring 244 has rotated the hub gear 130 and hub 104 clockwise and driven the jaws 62, 64, 66 to grip the light guide 18. The second shield 370 is free to rotate back to the open position and allow light to the light guide 18 under the influence of the shield springs 406, 408 as the dog pin 100 rotates back through the relieved portion 122 between the upper and lower shoulders 126, 124.

The motion of the jaws 62, 64, 66 as they close on the light guide 18 moves the pin 358 on the arm 350 back within the relatively unresponsive portion of the pin 358 and pin follower slot 338 engagement. Thus, the first shield 330 remains rotated away from blocking the opening 16 as long as a light guide 18 is gripped in the jaws. If the light guide 18 is pulled from the jaws while the mechanism is in this position, the jaws and first shield 330 will snap to the closed position. Because the jaws and first shield 330 are mechanically linked, there is no delay between jaw closure and first shield 330 closure and the user is protected from exposure to bright light from the light source 10.

Figure 28:
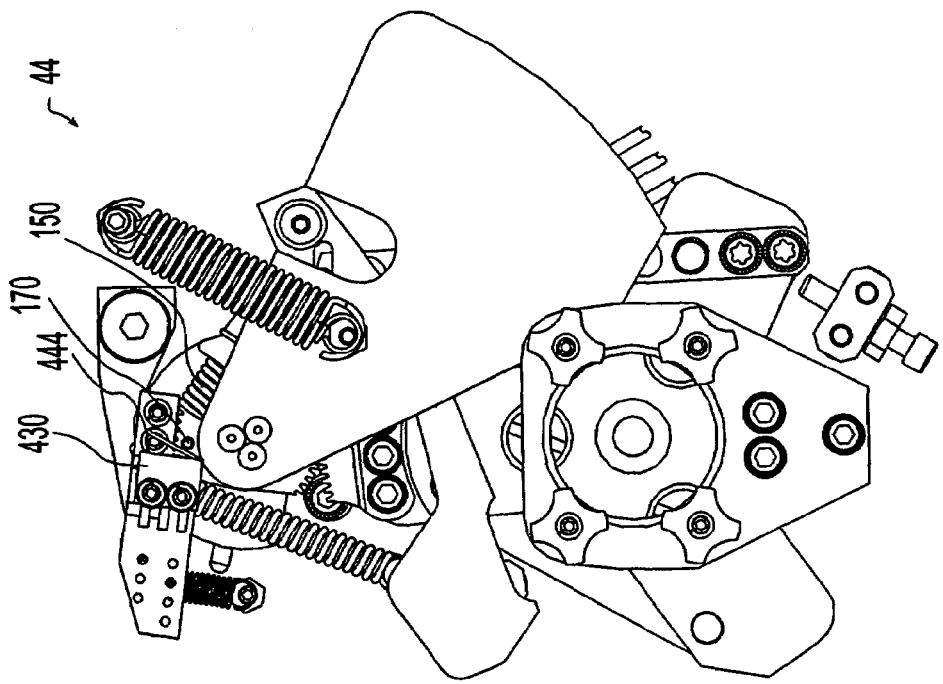
FIG. 28 is a back plan view of the fully assembled light guide receptacle of FIG. 3 in the same operating position as FIG. 27.
Figure 27:
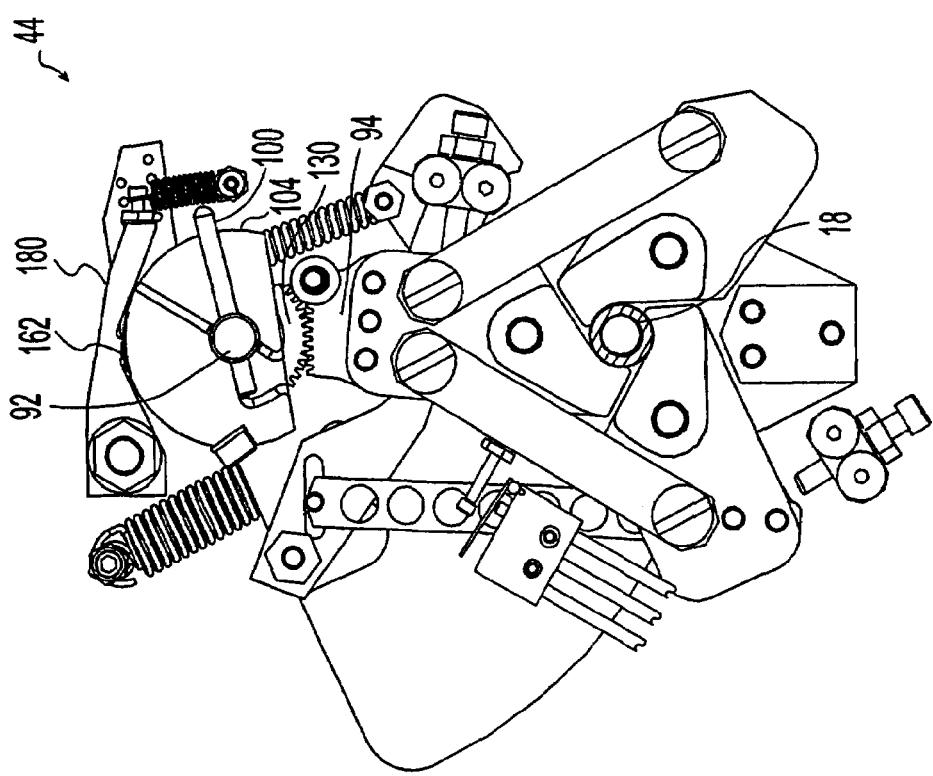
FIG. 27 is a front plan view of the fully assembled light guide receptacle of FIG. 3 (with certain elements omitted to aid visualization) in one operating position.

Referring to FIGS. 27 and 28, the drive shaft 92, dog pin 100, and hub 104 have been rotated further clockwise to engage the locking mechanism and increase the gripping pressure of the jaws 62, 64, 66 on the light guide 18. The hub gear 130, jaw gear 94, and jaws 62, 64, 66 remain stationary because the jaws are abutting the light guide 18. Therefore, the hub 104 rotates relative to the hub gear 130 and compresses the lock spring 150 causing an increase in the closure force exerted on the hub gear 130. This increased force is transmitted through the mechanism to the jaws 62, 64, 66 to increase the grip of the jaws 62, 64, 66 on the light guide 18. As the hub 104 is rotated clockwise, the pawl 180 engages the ratchet teeth 162 on the hub to prevent it from slipping back. The motion of the hub 104 relative to the hub gear 130, moves the lock switch 430 mounted on the hub 104 away from the lock switch pin 170 mounted on the hub gear 130 allowing the lock switch treadle 444 to move and actuate the switch. As discussed relative to the jaw switch 264, the lock switch 430 may be connected to the rest of the light source 10 to control a light source 10 function upon lock engagement. The lock switch 430 may be connected directly to a light source function or it may be connected to a controller. For example, in one embodiment, the controller 52 may respond to operation of the lock switch 430 to turn on an indicator 36 to indicate the locked condition to a user.

Although examples of a medical light source and its use have been described and illustrated in detail, it is to be understood that the same is intended by way of illustration and example only and is not to be taken by way of limitation. Accordingly, variations in and modifications to the medical light source and its use will be apparent to those of ordinary skill in the art, and the following claims are intended to cover all such modifications and equivalents.

What is claimed is:

1. A medical light source for providing light to a medical treatment site via a light guide, the medical light source comprising:
    a light guide receptacle, the light guide receptacle defining an opening with a perimeter, the opening perimeter being expandable and shrinkable between an open condition in which the opening is larger than the light guide, a closed condition in which the opening is the same size as the light guide and the perimeter of the opening grips the light guide with a first gripping pressure, and a locked condition in which the perimeter of the opening grips the light guide with a second, greater gripping pressure;
    an actuator operably connected to the light guide receptacle, the actuator being responsive to a user input to lock the opening perimeter in the locked condition.

2. The medical light source of claim 1 wherein the actuator is responsive to a user input to move the opening perimeter between the open, closed, and locked conditions.

3. The medical light source of claim 1 wherein the opening defines an axis, the light guide receptacle further comprising a plurality of jaws mounted for movement radially inwardly and outwardly relative to the opening axis, the jaws defining the perimeter of the opening.

4. The medical light source of claim 3 further comprising:
    a resilient member operably connected to the jaws to bias the jaws from a radially outward position corresponding to the open condition toward a radially inward position corresponding to the closed condition.

5. The medical light source of claim 4 further comprising:
    a ratchet mechanism, the actuator being operable to increase the gripping pressure incrementally between the first gripping pressure and the second gripping pressure, the ratchet mechanism being operable to maintain each incremental pressure increase absent a user input.

6. The medical light source of claim 5 further comprising:
    a second resilient element operably connected to the jaws, the actuator being operable to deform the second resilient element to transmit incrementally increasing gripping pressure to the jaws through the second resilient element.

7. The medical light source of claim 1 further comprising:
a light producing element mounted in light communicating relationship with the light guide receptacle;
a shutter mounted between the light producing element and the opening, the shutter being operable to control the amount of light transmitted to the opening; and
a sensor operably connected to the light guide receptacle and the shutter, the sensor being operable to produce a signal in response to movement of the opening perimeter to control operation of the shutter.

8. The medical light source of claim 1 further comprising:
an indicator;
a sensor operably connected to the light guide receptacle and the indicator, the sensor being operable to produce a signal in response to the opening perimeter being in the locked condition to control operation of the indicator.

9. The medical light source of claim 1 further comprising:
a light producing element mounted in light communicating relationship with the light guide receptacle; and
a first shield movable between a first shield light blocking position in which it blocks light from the light producing element from reaching the opening and a first shield light passing position in which it allows light to reach the opening.

10. The medical light source of claim 9 wherein the opening perimeter further has a rest condition corresponding to a nominal condition of the light guide receptacle with no user input and no light guide engaged with the opening, the light source further comprising a light guide receptacle mechanism operably connected to the first shield, the light guide receptacle mechanism being operable to position the first shield in the first shield light blocking position when the light guide receptacle is in the rest condition and the light guide receptacle mechanism being operable to position the first shield in the first shield light passing position when the light guide receptacle is in the closed condition.

11. The medical light source of claim 10 further comprising a second shield movable between a second shield light blocking position in which it blocks light from the light producing element from reaching the opening and a second shield light passing position in which it allows light to reach the opening, the second shield being operably connected to the light guide receptacle mechanism, the light guide receptacle mechanism being operable to position the second shield in the second shield light blocking position when the light guide receptacle is in the open condition and the light guide receptacle mechanism being operable to position the second shield in the second shield light passing position when the light guide receptacle is in the closed condition.

* * * * *